(12) United States Patent
Cheng et al.

(10) Patent No.: US 12,033,327 B2
(45) Date of Patent: Jul. 9, 2024

(54) METHODS, SYSTEMS AND APPARATUS FOR PROCESSING MEDICAL CHEST IMAGES

(71) Applicant: Shanghai United Imaging Intelligence Co., Ltd., Shanghai (CN)

(72) Inventors: Jie-Zhi Cheng, Shanghai (CN); Qitian Chen, Shanghai (CN)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 707 days.

(21) Appl. No.: 17/221,160

(22) Filed: Apr. 2, 2021

(65) Prior Publication Data
US 2021/0312629 A1    Oct. 7, 2021

(30) Foreign Application Priority Data

Apr. 7, 2020  (CN) .......................... 202010264187.1

(51) Int. Cl.
*G06T 7/11*    (2017.01)
*G06T 7/00*    (2017.01)
(Continued)

(52) U.S. Cl.
CPC .............. *G06T 7/11* (2017.01); *G06T 7/0012* (2013.01); *G16H 30/40* (2018.01); *G16H 50/20* (2018.01);
(Continued)

(58) Field of Classification Search
CPC ....... G06T 7/0012; G06T 7/0014; G06T 7/11; G06T 7/70; G06T 2207/10116;
(Continued)

(56) References Cited

U.S. PATENT DOCUMENTS 10,691,980 B1 *   6/2020   Guendel .................. G06T 7/70
10,751,016 B2     8/2020   Young et al.
(Continued)

FOREIGN PATENT DOCUMENTS

CN    108348208 A    7/2018
CN    109785303 A    5/2019

OTHER PUBLICATIONS

Wang et al., "Deep Convolutional Neural Network with Segmentation Techniques for Chest X-Ray Analysis", 2019 14th IEEE Conference on Industrial Electronics and Applications (ICIEA), pp. 1212-1216 (Year: 2019).*

*Primary Examiner* — Ping Y Hsieh
*Assistant Examiner* — Jose M Torres
(74) *Attorney, Agent, or Firm* — Zhong Law LLC

(57) ABSTRACT

Described herein are systems, methods, and instrumentalities associated with processing medical chest images such as chest X-ray (CXR) images. Segmentation models derived via a deep learning process are used to segment the chest images and obtain a rib segmentation result and a lung segmentation result for each image. The rib segmentation result may include a rib sequence identified in the image while the lung segmentation result may include one or more lung fields identified in the image. The quality of each chest image (e.g., whether the image reflects a breath-holding state of the patient) may then be determined based on whether a sufficient number of ribs in the rib segmentation result overlap with the lung fields in the lung segmentation result. The segmentation results may be obtained in a coarse-to-fine manner, e.g., by first determining a large rib area and then further segmenting the large rib area to identify each individual rib.

18 Claims, 10 Drawing Sheets

(51) Int. Cl.
 *G16H 30/40* (2018.01)
 *G16H 50/20* (2018.01)
(52) U.S. Cl.
 CPC ............... *G06T 2207/10116* (2013.01); *G06T 2207/20081* (2013.01); *G06T 2207/20084* (2013.01); *G06T 2207/30008* (2013.01); *G06T 2207/30061* (2013.01); *G06T 2207/30168* (2013.01)
(58) Field of Classification Search
 CPC . G06T 2207/20081; G06T 2207/20084; G06T 2207/30008; G06T 2207/30061; G06T 2207/30168; G16H 30/40; G16H 50/20
 See application file for complete search history.

(56) References Cited

U.S. PATENT DOCUMENTS

| | | | |
|---|---|---|---|
| 2006/0004282 A1* | 1/2006 | Oosawa | G06T 7/0012 600/416 |
| 2011/0052018 A1* | 3/2011 | Blaffert | G06T 7/149 382/128 |
| 2013/0108135 A1* | 5/2013 | Huo | G06T 7/12 382/132 |
| 2017/0109893 A1* | 4/2017 | Cong | A61B 6/5258 |
| 2017/0224302 A1* | 8/2017 | Von Berg | A61B 6/466 |
| 2018/0325481 A1* | 11/2018 | Young | A61B 6/5217 |
| 2020/0118043 A1* | 4/2020 | Venkataramani | G06F 16/5838 |
| 2020/0258215 A1* | 8/2020 | Kashyap | G06V 10/82 |
| 2020/0327660 A1* | 10/2020 | Katouzian | G06T 7/11 |
| 2021/0150710 A1* | 5/2021 | Hosseinzadeh Taher | G06V 10/764 |
| 2021/0303928 A1* | 9/2021 | Xu | A61B 5/7475 |

\* cited by examiner

METHODS, SYSTEMS AND APPARATUS FOR PROCESSING MEDICAL CHEST IMAGES

CROSS-REFERENCE TO RELATED APPLICATIONS

This application claims the benefit of Chinese Patent Application No. 2020102641871, filed Apr. 7, 2020, the disclosure of which is incorporated herein by reference in its entirety.

TECHNICAL FIELD

The present disclosure relates to the field of medical imaging, in particular to methods, systems, and apparatus for processing medical chest images such as chest X-ray (CXR) images.

BACKGROUND

Chest examinations (e.g., via a chest X-ray test) are common medical examination procedures. Using modern chest imaging technologies, sites such as the thorax, pleura, trachea, bronchus, lungs, cardiovascular systems, and/or the like may be checked and diagnosed. Effective control over the quality of chest imaging procedures such as chest X-ray (CXR) procedures may facilitate the accuracy of clinical diagnoses.

Chest imaging protocols generally require that a subject take a deep breath and hold the breath while chest images are being captured. With the subject in a state of deep inspiration, lung fields displayed on a chest image such as a CXR image are clearer and may better display lung tissues and/or pathological changes in the lungs. In practice, whether a chest image meets a quality standard may be determined by counting the number of ribs that overlap with the lung fields in the image. Subjects with insufficient inspiration are advised to retake the imaging procedure.

Currently, in the related art, whether a subject is in a proper breath-holding state while a chest image is taken is evaluated manually by a technician or doctor. However, as hospitals may need to perform a large number of imaging procedures every day and it is time-consuming to manually determine the number of ribs overlapping with the lung fields in each chest image, evaluating the quality of chest images according to relevant protocols becomes a difficult task, leading to poor imaging quality and low processing speed. No effective solution has been proposed thus far.

SUMMARY

Methods, systems, instrumentalities as well as a readable storage medium are described herein for processing a chest image such as a chest X-ray (CXR) image to solve problems faced by traditional CXR imaging methods (e.g., with respect to at least effectiveness and speed).

In a first aspect, the present application provides a method for processing a chest image, and the method may include the following steps: acquiring a chest image (e.g., which may be produced by a medical imaging device); providing the chest image to a machine-learned (e.g., preset) rib segmentation model to obtain a rib segmentation result that may indicates a rib sequence identified in the chest image; providing the chest image to a machine-learned (e.g., preset) lung field segmentation model to obtain a lung field segmentation result that may indicate one or more lung fields identified in the chest image; determining, based on the rib segmentation result and the lung field segmentation result, whether a predetermined set of one or more specific ribs overlap with the one or more lung fields in the chest image; and determining a quality of the chest image (e.g., whether the scan subject was in breath-holding state while the chest image was taken) in accordance with whether the one or more specific ribs overlap with the one or more lung fields in the chest image.

In some embodiments, the step of determining the quality of the chest image may include determining that the quality of the chest image meets a quality requirement if the one or more specific ribs overlap with the one or more lung fields, and determining that the quality of the chest image does not meet the quality requirement if the one or more specific ribs do not overlap with the one or more lung fields.

In some embodiments, the step of determining the quality of the chest image may include determining a number of ribs that overlap with the lung fields, and determining that the quality of the image meets a quality requirement if the number of ribs that overlap with the one or more lung fields is within a preset value range.

In some embodiments, the step of providing the chest image to the preset rib segmentation model to obtain the rib segmentation result may include the following: segmenting the chest image to determine a first region associated with a plurality of ribs identified in the chest image; segmenting the first region to determine one or more second regions, wherein each of the one or more second regions is associated with a respective subset of the plurality of ribs; and segmenting each of the one or more second regions to identify individual ribs located in the each of the one or more second regions.

In some embodiments, the rib segmentation model may be learned through at least the following steps: initializing parameters of the rib segmentation model; for each of a plurality of chest training images: segmenting the chest training image using the rib segmentation model and adjusting the parameters of the rib segmentation model based on a loss function that indicates a difference between an actual result of the segmentation and a desired result; determining that the loss function has converged; and responsive to determining that the loss function has converged, storing the parameters of the rib segmentation model.

In some embodiments, segmenting each of the chest training images using the rib segmentation model may include segmenting the chest training image using the rib segmentation model to determine a first rib area, wherein the first rib area is estimated to enclose a plurality of ribs in the chest training image; segmenting the first rib area using the rib segmentation model to determine one or more second rib areas, wherein each of the one or more second rib areas is estimated to enclose a respective subset of the plurality of ribs in the chest training image; and segmenting each of the one or more second rib areas using the segmentation model to determine one or more individual ribs within the each of the one or more second rib areas.

In some embodiments, the chest image may be obtained in real time while the medical imaging device configured to produce the chest image is in operation. After determining the quality of the chest image, the image and the corresponding image quality information may be stored in a database. Subsequently, upon receiving a review instruction, a preset condition for performing a quality review may be determined according to the review instruction, and one or more target images and/or quality information of the target images may be retrieved and/or reviewed from the database according to the preset condition.

In some embodiments, a determination may be made, e.g., at preset intervals, about whether an unprocessed chest image exists on a picture archive or a communication system (PACS) associated with a medical device. If the determination is that such an image exists, the image may be obtained and the quality of the image may be determined using the method described herein. The image and the quality information may then be stored in the database. Subsequently, a review instruction may be received and a preset condition for performing a quality review may be determined according to the review instruction. Based on the preset condition, one or more target chest images and/or quality information for the target images may be retrieved from the database and reviewed.

In a second aspect, the present application provides a system or apparatus for processing a chest image. Such a system or apparatus may include an image acquisition unit configured to obtain the chest image (e.g., from a medical imaging device), a rib segmentation unit configured to provide the chest image to a machine-learned (e.g., preset) rib segmentation model to obtain a rib segmentation result (e.g., which may include an identified rib sequence); a lung field segmentation unit configured to provide the chest image to a machine-learned (e.g., preset) lung field segmentation model to obtain a lung field segmentation result output by the lung-field segmentation model; and a quality evaluation unit configured to determine whether a predetermined set of one or more specific ribs overlap with the lung fields identified in the chest image, and further determine a quality of the chest image based on the overlap (or lack thereof).

In some embodiments, the quality evaluation unit may be configured to, based on a determination that one or more specific ribs overlap with the lung fields identified in the chest image, determine that the chest image is a qualified image. Conversely, if the one or more specific ribs do not overlap with the lung fields, the quality evaluation unit may be configured to determine that the chest image is a secondary image (e.g., having a quality lower than that of a qualified image).

In some embodiments, the quality evaluation unit is configured to, based on the number of specific ribs that overlap with the lung fields, determine that the chest image is a qualified image if the number of ribs overlapping with the lung fields is within a preset number or value range.

In some embodiments, the rib segmentation unit may be configured to segment the chest image to determine a first region associated with a plurality of ribs identified in the chest image, segment the first region to determine one or more second regions, wherein each of the one or more second regions is associated with a respective subset of the plurality of ribs, and segment each of the one or more second regions to identify individual ribs that are located within the each of the one or more second regions. Additionally, the rib segmentation unit may be further configured to determine a sequential order of the identified ribs.

In some embodiments, the system described herein may include a model configuration unit configured to learn the rib segmentation model via one or more of the following steps: initializing the parameters of the rib segmentation model; for each of a plurality of chest training images: segmenting the chest training image using the rib segmentation model and adjust the parameters of the rib segmentation model based on a loss function that indicates a difference between the result of the segmentation and a desired result; determining that the loss function has converged; and responsive to the determination that the loss function has converged, storing the parameters of the rib segmentation model.

In some embodiments, the model configuration unit may be configured to perform first segmentation, second segmentation, and third segmentation of each chest training image using the rib segmentation model according to different segmentation rules and standards. The model configuration unit may also be configured optimize the respective loss functions for the first, second, and third segmentations as well as a loss function (e.g., an end-to-end loss function) for the whole segmentation process (e.g., until the loss functions converge).

In some embodiments, the image acquisition unit may be configured to acquire a chest image in real time (e.g., during normal operation of a medical imaging device), and an information storage unit of the system described herein may be configured to store the chest image and the corresponding quality information for the image to a database. Subsequently, an image review unit of the system may receive a review instruction, determine a preset condition for the review according to the review instruction, and obtain one or more target chest images and quality information for the target images from the database according to the preset condition.

In some embodiments, the image acquisition unit described herein may be configured to determine, at preset intervals, whether an unprocessed chest image exists on a PACS of a medical device. If the determination is that such an image exists, the image acquisition unit may obtain the unprocessed chest image such that the quality of the image may be determined. Upon processing the chest image, the information storage unit described herein may be configured to store the image and the corresponding quality information to the database. Subsequently, the image reviewing unit described herein may be configured to receive a review instruction, determine a preset condition for the review according to the review instruction, and obtain one or more target chest images and/or quality information for the target images from the database according to the preset condition.

In a third aspect, the present application provides a readable storage medium having one or more executable programs stored thereon, wherein the executable programs may be executed by a processor to implement the steps of the above-mentioned methods for processing a chest image.

In a fourth aspect, the present application provides a device for processing a chest image. The device may include a memory for storing one or more executable programs, and a processor configured to, by executing the executable programs, implement the steps of the above-mentioned methods for processing a chest image.

Compared with related art, the methods, systems, instrumentalities as well as the readable storage medium described in the present application allow chest images to be obtained (e.g., during the normal operation of a medical imaging device) and the quality of the chest images to be determined using a machine-learned rib segmentation model and a machine-learned lung field segmentation model. A rib segmentation result produced by the rib segmentation model may include an identified rib sequence in the chest images while a lung field segmentation result produced by the lung field segmentation model may indicate one or more lung fields in the chest images. The quality of the chest images (e.g., whether the scan subject was in a breath-holding state) may be determined based on whether one or more specific ribs overlap with the lung fields, for example, by combining and comparing the two segmentation results. Using the techniques described herein, whether a scan subject is in a breath-holding state during a chest imaging procedure no longer needs to be evaluated by a doctor or technician, and may instead be determined directly using the quality control techniques described herein. As a result, the waiting time for patients may be shortened and the effectiveness and speed of chest imaging procedures may be improved.

Details of one or more embodiments of the present application are set forth in the accompanying drawings and the description below to make other features, objects and advantages of the present application more concise and understandable.

BRIEF DESCRIPTION OF THE DRAWINGS

The accompanying drawings are used to facilitate understanding of the present application, and constitute a part of the application. The embodiments illustrated and described herein are intended to explain the present application and not to form any limitation to the present application. In the accompanying drawings.

DETAILED DESCRIPTION

To make the objectives, technical solutions and advantages of the disclosure clearer, the disclosure is further explained in a greater detail in combination with the accompanying drawings and embodiments. It should be understood that the embodiments described here are only for explaining the disclosure, and not for limiting the scope of the disclosure.

As used in the application and the appended claims, the singular forms "a," "an," and "the" can also refer to plural nouns unless the relevant context clearly dictates otherwise. In general, the terms "include" and "comprise" are intended to encompass explicitly identified steps and/or elements, which do not constitute an exclusive list, and the concerned method or device may include other steps or elements.

Although the present application makes various references to certain modules in a system according to some embodiments of the present application, any number of different modules may be used and run on an imaging system and/or a processor. The modules are illustrative only, and different aspects of the systems and methods may use different modules.

Flowcharts are used in the present application to illustrate operations performed by a system according to embodiments of the present application. It should be understood that a preceding or subsequent operation may not be necessarily performed in that exact order. Instead, various steps may be processed in a reverse sequence and/or simultaneously. Moreover, other operations may also be added to a described procedure, or one or more steps may be removed from a described procedure.

Figure 1:
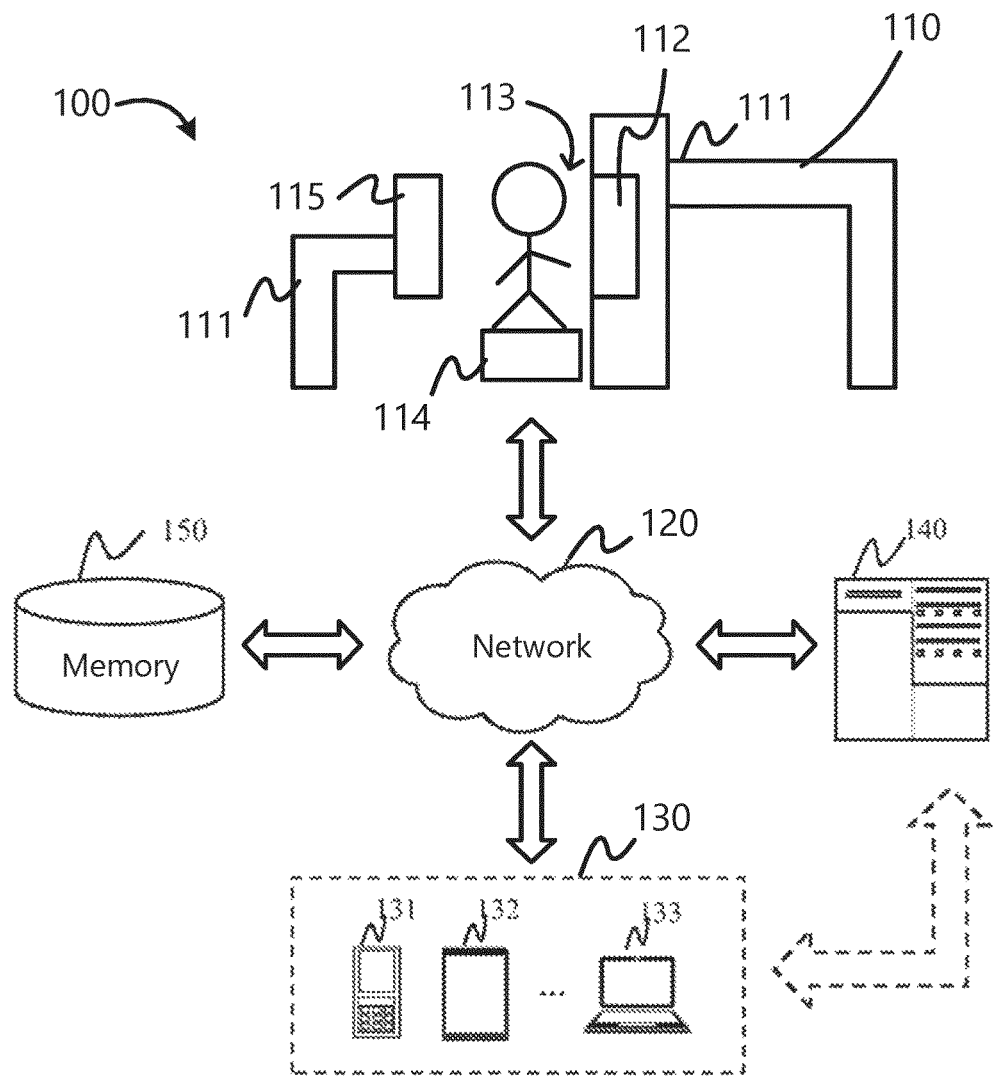
FIG. 1 is a schematic diagram of an example system 100 according to an embodiment described herein.

FIG. 1 is a schematic diagram of an example system 100 for processing a medical chest image (e.g., a chest X-ray (CXR) image) according to an embodiment described herein. As shown in FIG. 1, the system 100 may include a scanner 110, a network 120, one or more terminal devices 130, a processing engine 140, and a storage device 150. All of the devices and/or components in the system 100 may be interconnected (e.g., communicatively coupled together) by the network 120.

The scanner 110 may be configured to scan a subject (e.g., a patient) and generate imaging data (e.g., CXR data) associated with the scanned subject. In some embodiments, the scanner 110 may be a medical imaging device, such as a CXR imaging device. The "image" referred to in the present disclosure may include a 2D image, a 3D image, a 4D image and/or other related data, the type of which should not limit the scope of the present disclosure. Various modifications and alterations may be made by those skilled in the art in light of the present disclosure. The scanner 110 may include a frame 111 and a detector 112, and may be associated with a detection region 113 and a platform 114. In some embodiments, the scanner 110 may further include a radioactive scanning source 115. The frame 111 may be configured to support the detector 112 and/or the radioactive scanning source 115. The scan subject may be positioned on the platform 114 for scanning, and the radioactive scanning source 115 may emit radioactive rays towards the scan subject. The detector 112 may detect radiation events (e.g., X-rays) emitted from the detection region 113. In some embodiments, the scanner 110 may include an X-ray scanning device and the detector 112 may include a circuit for detecting and receiving signals (e.g., radioactive signals).

The network 120 may include any suitable network capable of assisting the system 100 in exchanging information and/or data. In some embodiments, one or more components (e.g., the scanner 110, the terminal device 130, the processing engine 140, the storage 150, etc.) of the system 100 may communicate information and/or data with one or more other components of the system 100 through the network 120. For example, the processing engine 140 may obtain image data from the scanner 110 through the network 120. As another example, the processing engine 140 may obtain user instructions from the terminal device 130 through the network 120. The network 120 may include a public network (e.g., the Internet), a private network (e.g., a local area network (LAN), a wide area network (WAN), etc.), a wired network (e.g., Ethernet), a wireless network (e.g., an 802.11 network, a Wi-Fi network, etc.), a cellular network (e.g., a long term evolution (LTE) network), a frame relay network, a virtual private network ("VPN"), a satellite network, a telephone network, a router, a hub, a switch, a server computer, and/or any combination thereof. By way of example only, the network 120 may include a cable network, a wired network, a fiber-optic network, a telecommunication network, an intranet, a wireless local area network (WLAN), a metropolitan area network (MAN), a public switched telephone network (PSTN), a Bluetooth network, a ZigBee network, a near field communication (NFC) network, etc., or any combination thereof. In some embodiments, the network 120 may include one or more network access points. For example, the network 120 may include wired and/or wireless network access points, such as base stations and/or Internet exchange points, through which one or more components of the medical device 100 may be connected to the network 120 to exchange data and/or information.

The one or more terminals devices 130 may include a mobile device 131, a tablet computer 132, a notebook computer 133, etc., or any combination thereof. In some embodiments, the mobile device 131 may include a smart home device, a wearable device, a mobile device, a virtual reality device, an augmented reality device, etc., or any combination thereof. In some embodiments, the smart home device may include a smart lighting device, a control device for a smart appliance, a smart surveillance device, a smart television, a smart camera, an Internet phone, etc., or any combination thereof. In some embodiments, the wearable device may include a bracelet, footwear, glasses, a helmet, a watch, clothing, a backpack, smart jewelry, etc., or any combination thereof. In some embodiments, the mobile device 131 may include a mobile phone, a personal digital assistant (PDA), a gaming device, a navigation device, a point of sale (POS) device, a notebook computer, a tablet computer, a desktop computer, etc., or any combination thereof. In some embodiments, the virtual reality device and/or the augmented reality device may include a virtual reality helmet, virtual reality glasses, virtual reality eye shields, an augmented reality helmet, augmented reality glasses, augmented reality eye shields, etc., or any combination thereof. For example, the virtual reality device and/or the augmented reality device may include a Google Glass, an Oculus Rift, Hololens, a Gear VR, or the like. In some embodiments, the terminal device 130 may be a part of the processing engine 140.

The processing engine 140 may be configured to process data and/or information obtained from the scanner 110, the terminal 130, and/or the storage device 150. In some embodiments, the processing engine 140 may be a single server or a server group (e.g., one or more servers interconnected via the network 120). The server group may be centralized or distributed. In some embodiments, the processing engine 140 may be local or remote to the other devices or components of the system 100. For example, the processing engine 140 may access the information and/or data stored in or produced by the scanner 110, the terminal device 130, and/or the storage device 150 through the network 120. As another example, the processing engine 140 may be directly connected to the scanner 110, the terminal device 130, and/or the storage device 150 to access the information and/or data stored therein. In some embodiments, the processing engine 140 may be implemented on a cloud platform. By way of example only, the cloud platform may include a private cloud, a public cloud, a hybrid cloud, a community cloud, a distributed cloud, an Internet cloud, a multi-cloud, etc., or any combination thereof. In some embodiments, the processing engine 140 may be implemented by a computing device 200 including one or more components as shown in FIG. 2.

The storage device 150 may be configured to store data (e.g., chest imaging data), instructions, and/or any other information. In some embodiments, the storage device 150 may store data obtained from the terminal device 130 and/or the processing engine 140. In some embodiments, the storage device 150 may store data and/or instructions which may be executed or used by the processing engine 140 to perform the example methods described by the present disclosure. In some embodiments, the storage device 150 may include a mass storage device, a removable storage device, a volatile read-write memory, a read-only memory (ROM), etc., or any combination thereof. The example mass storage device may include a magnetic disk, an optical disk, a solid state drive, or the like. The example removable memory may include a flash drive, a floppy disk, an optical disk, a memory card, a compact disk, a magnetic tape, or the like. The example volatile read-write memory may include a random access memory (RAM). The example RAM may include a dynamic RAM (DRAM), a double data rate synchronous dynamic RAM (DDR SDRAM), a static RAM (SRAM), a thyristor RAM (T-RAM), a zero capacitor RAM (Z-RAM), or the like. The example ROM may include a mask ROM (MROM), a programmable ROM (PROM), an erasable programmable ROM (EPROM), an electrically erasable programmable ROM (EEPROM), an optical disk ROM (CD-ROM), a digital versatile disk ROM, or the like. In some embodiments, the storage device 150 may be implemented on a cloud platform. By way of example only, the cloud platform may include a private cloud, a public cloud, a hybrid cloud, a community cloud, a distributed cloud, an Internet cloud, a multi-cloud, etc., or any combination thereof.

In some embodiments, the storage device 150 may be connected to the network 120, so as to communicate with one or more other components (e.g., the processing engine 140, the terminal device 130, etc.) in the system 100. One or more devices or components in the system 100 may access the data or instructions stored in the storage device 150 through the network 120. In some embodiments, the storage device 150 may be directly connected to or configured to communicate with one or more other components (e.g., the processing engine 140, the terminal device 130, etc.) in the system 100. In some embodiments, the storage device 150 may be a part of the processing engine 140.

Figure 2:
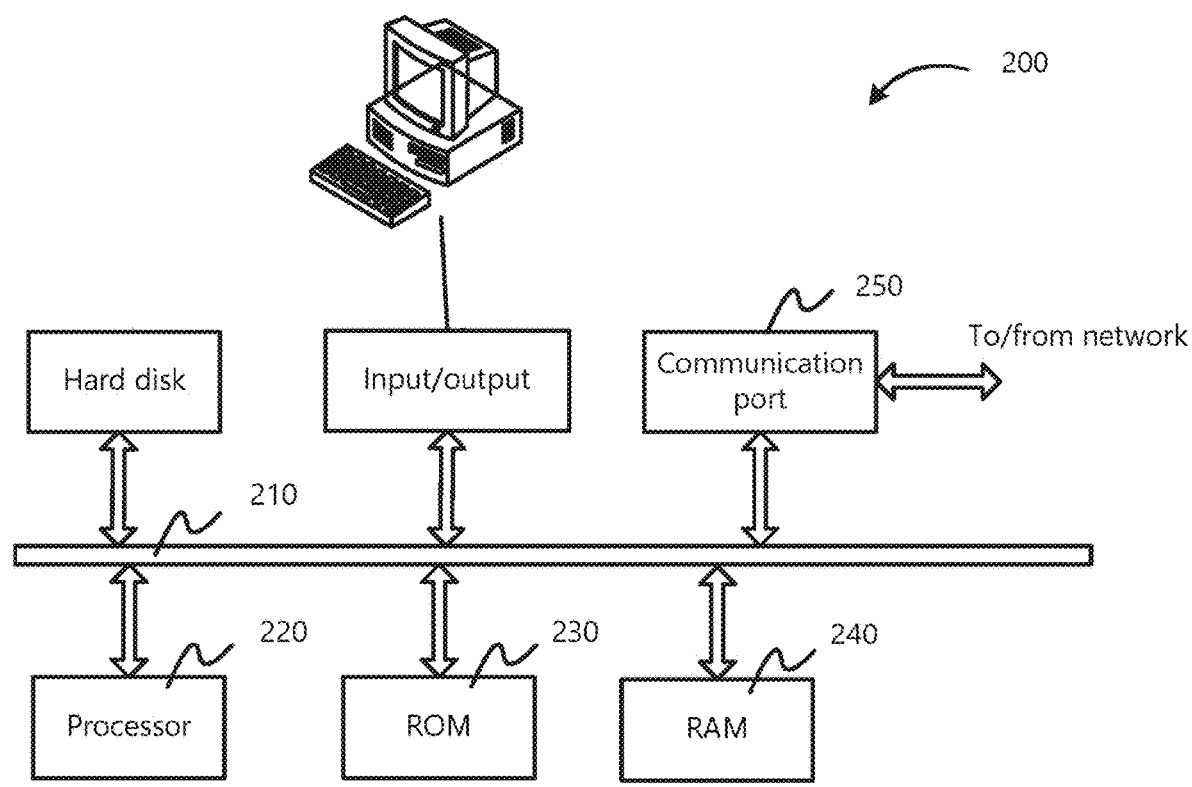
FIG. 2 is a schematic diagram of example hardware and/or software components of an example computing device 200 on which a processing engine 140 shown in FIG. 1 may be implemented according to an embodiment described herein.

FIG. 2 is a schematic diagram of example hardware and/or software components of an example computing device 200 on which the processing engine 140 may be implemented according to an embodiment described herein. As shown in FIG. 2, the computing device 200 may include an internal communication bus 210, a processor 220, a read-only memory (ROM) 230, a random access memory (RAM) 240, a communication port 250, an input/output component (not shown), a hard disk (not shown), and/or a user interface (not shown).

The internal communication bus 210 may be configured to realize data communication among the components of the computing device 200. The processor 220 may be configured to execute computer instructions (e.g., program codes) and perform the functions of the processing engine 140 in accordance with the techniques described herein. The computer instructions may include, for example, routines, programs, scanned objects, components, data structures, procedures, modules, and/or functions which, standing alone or in combination, perform one or more particular functions described herein. For example, the processor 220 may process image data obtained from the scanner 110, the terminal device 130, the storage device 150, and/or any other component of the system 100 shown in FIG. 1. In some embodiments, the processor 220 may include one or more processors (e.g., hardware processors), such as microcontrollers, microprocessors, reduced instruction set computers (RISC), application specific integrated circuits (ASIC), application specific instruction set processors (ASIP), central processing units (CPU), graphics processing units (GPU), physical processing units (PPU), microcontroller units, digital signal processors (DSP), field programmable gate arrays (FPGA), advanced RISC machines (ARM), programmable logic devices (PLD), any circuit or processor capable of executing one or more functions, or the like, or any combination thereof.

For illustration purposes only, only one processor 220 is shown and described with the computing device 200. However, it should be noted that the computing device 200 in the present disclosure may include multiple processors, and therefore, the operations and/or method steps described in the present disclosure as being performed by one processor may also be performed by multiple processors jointly or separately.

The ROM 230 and the RAM 240 may be configured to store the data/information obtained from the scanner 110, the terminal device 130, the storage device 150, and/or any other component of the system 100. The ROM 230 may include a mask ROM (MROM), a programmable ROM (PROM), an erasable programmable ROM (EPROM), an electrically erasable programmable ROM (EEPROM), an optical disk ROM (CD-ROM), a digital versatile disk ROM, or the like. The RAM 240 may include a dynamic RAM (DRAM), a double data rate synchronous dynamic RAM (DDR SDRAM), a static RAM (SRAM), a thyristor RAM (T-RAM), a zero capacitor RAM (Z-RAM), or the like. In some embodiments, the ROM 230 and the RAM 240 may store one or more programs and/or instructions for performing the example methods described in the present disclosure.

The communication port 250 may be connected to a network (e.g., the network 120) to facilitate data communication to and from the computing device 200. For example, the communication port 250 may be configured to establish a connection between the processing engine 140 and the scanner 110, the terminal device 130, and/or the storage device 150. The connection may be a wired connection, a wireless connection, any other communication connection capable of realizing transmission and/or reception of data, and/or any combination of these connections. The wired connection may include, for example, an electrical cable, an optical cable, a telephone line, etc., or any combination thereof. The wireless connection may include, for example, a Bluetooth link, a Wi-Fi link, a WiMax link, a WLAN link, a ZigBee link, a mobile network link (e.g., 3G, 4G, 5G, etc.), or the like, or combinations thereof. In some embodiments, the communication port 250 may be a standard communication port, such as RS232, RS485, or the like. In some embodiments, the communication port 250 may be designed specially to perform the functions described herein. For example, the communication port 250 may be designed in accordance with a digital imaging and communications in medicine (DICOM) protocol.

The input/output component described herein may support input/output data flow between the computing device 200 and other components. In some embodiments, the input/output component may include an input device and an output device. Examples of the input device may include a keyboard, a mouse, a touch screen, a microphone, etc., or combinations thereof. Examples of the output device may include a display device, a speaker, a printer, a projector, etc., or combinations thereof. Examples of the display device may include a liquid crystal display (LCD), a light emitting diode (LED) based display, a flat panel display, a curved screen, a television device, a cathode ray tube (CRT), a touch screen, etc., or combinations thereof.

The computing device 200 may also include various forms of program storage units and data storage units, such as one or more hard disks, which may be configured to store various data files used in computation and/or communication, as well as possible program instructions to be executed by the processor 220. The user interface described herein may realize interaction and information exchange between the computing device 200 and a user.

Figure 3:
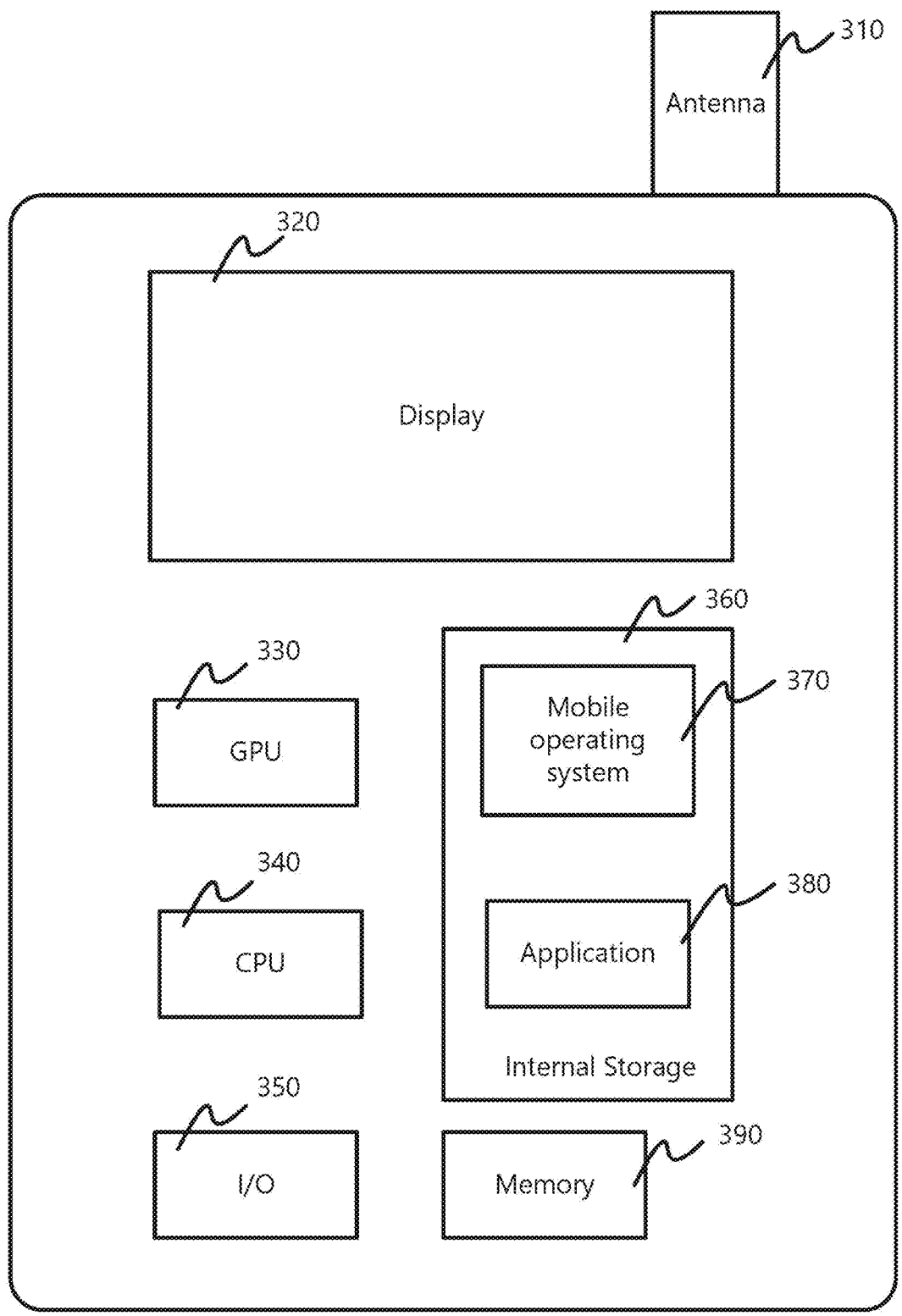
FIG. 3 is a schematic diagram of example hardware and/or software components of an example mobile device 300 on which a terminal 130 shown in FIG. 1 may be implemented according to an embodiment described herein.

FIG. 3 is a schematic diagram of example hardware and/or software components of an example mobile device 300 that may be configured to operate as the terminal device 130 according to an embodiment described herein. As shown in FIG. 3, the mobile device 300 may include an antenna 310, a display 320, a graphics processing unit (GPU) 330, a central processing unit (CPU) 340, an input-output unit (I/O) 350, an internal storage 360, and/or a memory 390. In some embodiments, the mobile device 300 may also include other suitable components, including, but not limited to, a system bus or a controller (not shown). In some embodiments, a mobile operating system 370 (e.g., iOS, Android, Windows Phone, etc.) and one or more applications 380 may be loaded from the memory 390 into the internal storage 360 for execution by the CPU 340. The application 380 may include a browser or any other suitable mobile application for receiving and rendering information related to an image processing operation or other information from the processing engine 140. User interaction with information flow may be realized through the I/O 350 and provided to the processing engine 140 and/or other components of the system 100 through the network 120.

To implement the various modules, units, and functions described in the present disclosure, a computer hardware platform may be used as the hardware platform(s) for one or more of the devices, components, or elements described herein. A computer with a user interface element may be used as a personal computer (PC) or any other type of workstation or terminal device. The computer may also act as a server if programmed suitably. Methods, systems, instrumentalities, or the like, for processing a medical chest image (e.g., a CXR image) may be implemented in the system 100 shown in FIG. 1.

Figure 4:
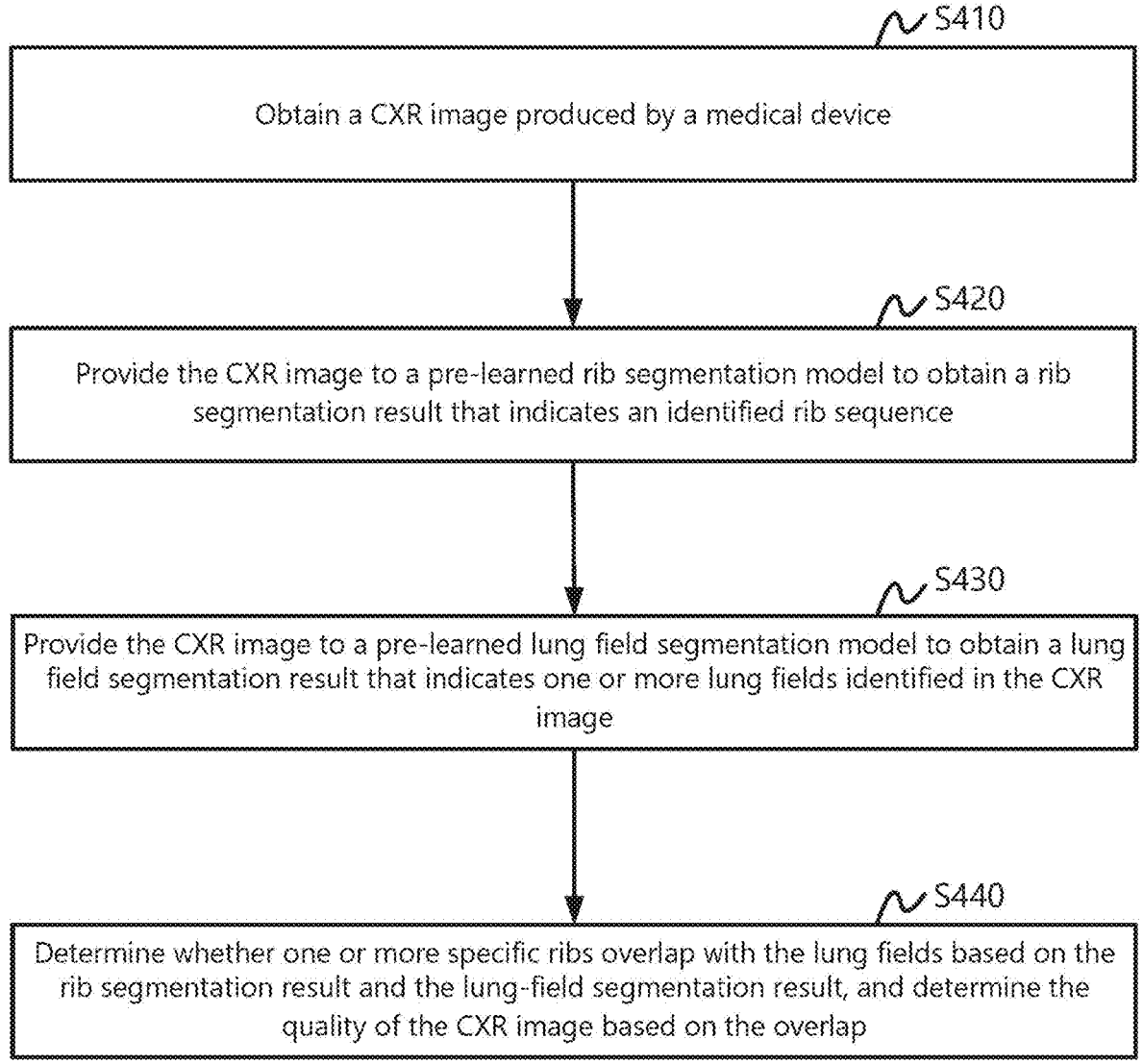
FIG. 4 is a flowchart of an example method for processing a chest image (e.g., a chest X-ray (CXR) image) according to an embodiment described herein.

FIG. 4 is a schematic flowchart of an example method for processing a chest image (e.g., a CXR image) according to an embodiment described herein. The method may include one or more of the following steps:

At S410, a CXR image produced by a medical device such as an X-ray scanner may be obtained. For example, in this step, a subject (e.g., a patient) to be scanned may step onto the platform 114 of the scanner 110 shown in FIG. 1 so as to enter the detection range of the scanner 110. A scanning operation may then be performed on the subject and a CXR image produced therefrom may be stored in the storage device 150 shown in FIG. 1.

At S420, the CXR image may be provided to a preset rib segmentation model to obtain a rib segmentation result. The rib segmentation result may indicate one or more ribs identified in the CXR image and/or a sequential order (e.g., an identified rib sequence) of the one or more identified ribs. For example, the rib segmentation result may include a segmentation map that indicates the locations and/or contours of the ribs and/or labelling that indicates respective sequence numbers associated with the identified ribs (e.g., rib1, rib2 . . . rib12).

The rib segmentation model may be a machine-learned (e.g., deep learning-based) segmentation model pre-trained on the processing engine 140 or a similar device, and stored (e.g., implemented) in the processing engine 140. The rib segmentation model may be trained (e.g., offline) on a large amount of chest imaging data and as such is capable of accurately segmenting and/or labeling a rib sequence (e.g., at an inference time) based on an input CXR image. For example, when the CXR image includes multiple ribs, the rib segmentation model may be able to (e.g., directly) identify and differentiate the ribs with fine details.

At S430, the CXR image may be provided to a preset lung field segmentation model to obtain a lung field segmentation result. The lung field segmentation model may be a machine-learned (e.g., deep learning-based) segmentation model pre-trained on the processing engine 140 or a similar device, and stored (e.g., implemented) in the processing engine 140. The rib segmentation model may be trained (e.g., offline) on a large amount of chest imaging data and as such is capable of accurately segmenting (e.g., directly at an inference time) one or more lung fields from the CXR image and indicating the one or more lung fields in the lung-field segmentation result.

At S440, a determination may be made regarding an amount of overlap between the one or more ribs identified in the CXR image and the one or more lung fields identified in the CXR image. The determination may be made, for example, based on the rib segmentation result and the lung field segmentation result described herein. Responsive to determining the amount of overlap, a further determination regarding the quality of the CXR image may be made according to the amount of overlap.

As described herein, the rib segmentation result may indicate the locations (e.g., distribution positions) of the ribs, the sequential order of the ribs, or the like, and the lung field segmentation result may indicate the locations (e.g., distribution regions) of the lung fields. Therefore, whether the ribs overlap with the lung fields may be determined according to the respective locations of the ribs and the lung fields. In addition, since the rib segmentation result may also indicate a sequential order of the ribs, a determination may be made regarding whether one or more specific ribs (e.g., rib1, rib2, . . . rib 10, etc., which may be preconfigured) overlap with the lung fields. This way, the quality of a CXR image may be determined quickly and accurately (e.g., at an inference time) based on whether a specific set of ribs (e.g., the set may be predetermined) overlap with the lung fields.

As described herein, a chest image (e.g., a CXR image) may be obtained from a medical device such as an X-ray scanner. The CXR image may be provided to a rib segmentation model and a lung field segmentation model, respectively, so as to obtain a rib segmentation result and a lung field segmentation result, respectively. The rib segmentation result may indicate an identified rib sequence (e.g., one or more ribs and their respective sequence numbers) identified in the CXR image, while the lung field segmentation result may indicate one or more lung fields identified in the CXR image. An amount of overlap between the ribs (e.g., one or more specific ribs preset by a user) and the lung fields may be determined, for example, by combining and/or comparing the two segmentation results. The quality of the CXR image may then be determined based on the amount of overlap. By analyzing and processing CXR images using machine-learned (e.g., deep learning based) segmentation models, the quality of the CXR images (e.g., whether the images are taken at deep inspiration) may be quickly determined based on overlap between one or more ribs (e.g., a preconfigured set of specific ribs) and one or more lung fields in each of the CXR images. This may eliminate the need for doctors and/or technicians to manually evaluate the CXR images to determine their quality. As a result, the waiting time for imaging subjects as well as the quality and speed of the chest imaging operations may be improved.

It should be noted that the techniques described herein for processing a chest image (e.g., a CXR image) may be executed on a console of a medical device (e.g., an X-ray scanner), on a post-processing workstation associated with the medical device, on the example computing device 200 that may be configured to implement the processing engine 140, on the terminal device 130 that may be configured to communicate with the medical device, etc. The devices and/or entities on which these techniques may be implemented are not limited to the examples provided herein, and may be added or modified according to the needs of an actual application.

In addition, the rib segmentation model and/or the lung-field segmentation model may be implemented using an artificial neural network such as a convolutional neural network (CNN). The neural network may adopt an encoder-decoder architecture (e.g., including a lightweight encoder-decoder architecture similar to that adopted in LinkNet) and/or other types of suitable neural network architectures as a basic structure. In examples, the artificial neural network include an encoder network, which in turn may include a plurality of layers such as one or more convolutional layers, one or more pooling layers, and/or one or more fully connected layers. The convolutional layers of the neural network may include a plurality of convolution kernels or filters configured to extract specific features from an input image (e.g., a CXR image) via one or more convolution operations. The convolution operations may be followed by batch normalization and/or non-linear activation, and the features extracted by the convolutional layers (e.g., in the form of one or more feature maps) may be down-sampled through the one or more pooling layers (e.g., using a 2×2 window and a stride of 2) to reduce the redundancy and/or dimension of the features (e.g., by a factor of 2). As a result of the convolution and/or down-sampling operations, respective feature representations of the input image may be obtained, for example, in the form of a feature map or feature vector.

The artificial neural network may also include a decoder network, which in turn may include a plurality of layers such as one or more convolutional layers (e.g., transposed convolutional layers) and/or one or more un-pooling layers. Through these layers, the decoder network may perform a series of up-sampling and/or transposed convolution operations on the feature map(s) or feature vector(s) produced by the encoder network so as to decode the features extracted from the input image and restore them to the original image size or resolution. For example, the decoder network may up-sample the feature representations produced by the encoder network based on pooled indices stored by the encoder network. The decoder network may then process the up-sampled representations through one or more transposed convolution operations (e.g., using 3×3 transposed convolutional kernels with a stride of 2) and/or one or more batch normalization operations to obtain one or more dense feature maps (e.g., up-scaled by a factor of 2). The output of the decoder network may include a segmentation mask that delineates one or more regions corresponding to a lung field or a rib captured by the input image. In examples, such a segmentation mask may correspond to a multi-class, pixel/voxel-wise probabilistic maps in which pixels or voxels belonging to each of the multiple classes are assigned a probability value indicating the classification of the pixels/voxels. In the case of a two-dimensional (2D) input image, the output of the decoder network may indicate the boundary points of the delineated regions (e.g., corresponding to a rib or lung field), while in the case of a three-dimensional (3D) input image, the output of the decoder network may indicate 3D mesh surfaces associated with the delineated regions.

In at least some embodiments, a selection instruction may be received by the processing engine 140, for example, before a determination is made regarding whether one or more ribs overlap with a lung field (e.g., according to rib segmentation and lung field segmentation results. The selection instruction may indicate one or more target ribs (e.g., one or more ribs with specific sequence numbers) that are to be checked for overlap with the lung field. For example, the human body includes 12 ribs in the chest area and the selection instruction may indicate that a specific site or rib area is the focus of checking. Such focus may be determined in advance (e.g., preset as a part of the system configuration and/or received via instruction by a doctor or technician). For instance, the selection instruction may indicate that the location of rib10 (e.g., the 10th rib) is the target location to check for overlap. Consequently, the 10th rib may be determined by the processing engine as the target rib for detailed checking and analysis.

In at least some embodiments, the quality of a CXR image may be determined as follows: if one or more specific ribs are determined to overlap with one or more lung fields, the CXR image may be determined (e.g., and indicated) as having a first quality (e.g., being a qualified CXR image); if the one or more specific ribs are determined to not overlap with the lung fields, the CXR image may be determined (e.g., and indicated) as having a second quality (e.g., being a secondary CXR image with a quality lower than that of the qualified CXR image).

In at least some embodiments, when a scan subject is in a breath-holding state, the lungs of the subject may be expanded, and one or more specific ribs of the subject should overlap with one or more lung fields of the subject captured in a CXR image. Accordingly, the quality of the CXR image may be determined based on whether the one or more specific ribs overlap with the lung fields. If the specific ribs overlap with the lung fields, a determination may be made that the scan subject was in the breath-holding state and the obtained CXR is a qualified CXR. If the specific ribs do not overlap with the lung fields, a determination may be made that the scan subject was not in a breath-holding state (e.g., including an insufficient breath-holding state) and the obtained CXR image is not a qualified CXR image (e.g., the quality of the image is lower than that of the qualified CXR and the CXR image is a secondary CXR image). By determining the quality of a CXR image based on detected overlap between specific ribs and lung fields, the techniques described herein may allow a doctor or technician to detect and resolve issues in the CXM image promptly (e.g., by asking the subject to be re-scanned) such that unnecessary scanning and waiting time may be reduced, and the doctor or technician may more effectively obtain physiological information about the scan subject.

In at least some embodiments, the quality of a CXR image may be determined as follows: if one or more specific ribs are determined to overlap with one or more lung fields, the number of ribs that overlap with the lung fields may be counted, and if the number is within a preset value range or number range, the CXR image may be determined (e.g., indicated) as a qualified CXR image.

In at least some embodiments, when a scan subject is in the breath-holding state, the lungs of the subject may be expanded, and a number of ribs (e.g., ribs with specific sequence numbers such as rib10) should overlap with one or more lung fields captured in a CXR image. Accordingly, the specific ribs that overlap with the lung fields may be counted and the counted number may be compared with a preset value or number range. If the number is within the preset value or number range, a determination may be made that the scan subject was in the breath-holding state and the obtained CXR image is a qualified CXR. The preset value or number range may be adjusted according to the needs of an actual application. If the counted number is outside the preset value or number range, the CXR image may be indicated as a secondary CXR image (e.g., with a quality lower than that of a qualified image).

In at least some embodiments, providing a chest image (e.g., a CXR image) to a pre-learned rib segmentation model to obtain a rib segmentation result may include one or more the following steps:

An initial estimation may be made to identify all ribs in the CXR image using the rib segmentation model and a first (e.g., primary) segmentation may be performed using the rib segmentation model to delineate a region where all the ribs are estimated to be located. Such a region may be labeled, for example, as a first or primary region. A second (e.g., secondary) segmentation may then be performed, using the rib segmentation model, on the first region (e.g., on all the ribs in the labelled first region) to obtain one or more second regions (e.g., rib set regions of different classes), where each of the one or more second regions is estimated to include a subset of the ribs in the first region. A third (e.g., tertiary) segmentation may then be performed on each of the second regions (e.g., on each of the rib set regions obtained via the second segmentation) to determine the region of each individual rib. Further, a sequential order of the ribs may be determined, for example, according to the position of each rib within a rib set region and the position of each rib set region in the CXR image. As such, the rib segmentation result may indicate the respective regions (e.g., bounds and/or contours) of the ribs captured in the CXR image and/or a sequential order of the ribs.

In these embodiments, the CXR image may be segmented multiple times using the rib segmentation model. For instance, an initial segmentation may identify, e.g., at a coarse level, a region where all the ribs in the CXR image may be located. Such a region may be segmented as a first labelled region. A second segmentation may then be performed on the first labelled region, through which the ribs in the labelled region may be divided into several groups each corresponding to a classified rib set region. Subsequently, a third segmentation may be further performed on each classified rib set region to determine the bounds and/or contours of each individual rib in the rib set region. The sequential order of the individual ribs may also be determined (e.g., the ribs may be sequentially arranged) according to the position of each rib within a corresponding rib set region and the position of the rib set region within the CXR image. This way, the ribs (e.g., the respective areas occupied by the ribs) in the CXR image may be distinguished from each other using the pre-learned rib segmentation model and the segmentation result may enjoy high accuracy despite the similarities among the ribs, since the task is accomplished via multiple segmentation operations, thus reducing the difficulty associated with each of the segmentation operations.

Further, while performing the second segmentation on the first region that is estimated to enclose all of the ribs in the CXR image, the groups or classes of ribs resulting from the second segmentation may be adjusted or set according to the needs of the actual application. For example, among the 12 ribs in the human chest, the 1st through the 6th ribs may be set as a first group or class, the 7th to the 10th ribs may be set as a second group or class, the 11th to the 12th ribs may be set as a third group or class, etc. Other manners of classification may also be applied.

In at least some embodiments, the rib segmentation model used to process the chest image (e.g., the CXR images) may be trained as followings. The rib segmentation model (e.g., which may be a multi-label segmentation model) may be assigned an initial set of parameters (e.g., weights associated with the various layers of the artificial neural network through which the model is implemented). The initial set of parameters may be obtained, for example, by sampling from a probability distribution or based on parameter values of an existing neural network having a similar architecture. A plurality of CXR sample images may be prepared to serve as a training dataset for the rib segmentation model. The preparation may include, for example, discarding images that are of poor quality, reformatting the images into a suitable format, converting color images to grayscale, resizing the images into unified dimensions, and/or the like. The training images may then be provided (e.g., as an input) to the rib segmentation model.

For each of the training images, a rib segmentation may be performed using the rib segmentation model (e.g., using existing parameters of the segmentation model) according to a predetermined set of segmentation rules (e.g., standards). A loss associated with the segmentation (e.g., a difference between the actual segmentation result and a ground truth) may be determined in accordance with a loss function. Such a loss function may be based on, for example, mean squared errors (MSE), L1/L2 norms, etc. Responsive to determining the loss, the parameters of the rib segmentation model may be optimized (e.g., adjusted to reduce the loss), for example, through a backpropagation process until the loss function converges. The loss function may be considered to have converged, for example, after a pre-determined number of training iterations have been completed, or if the change in the value of the loss function between two training iterations falls below a predetermined threshold. In examples, the backpropagation may be conducted based on a gradient descent (e.g., a stochastic gradient descent) associated with the loss function. Once the training is completed, the present parameters of the rib segmentation model may be stored and the rib segmentation model may be deployed to process medical chest images, as described herein.

As described herein, the initialized rib segmentation model (e.g., which may be a multi-label segmentation model) may be trained with a plurality of CXR sample images to obtain the rib segmentation model. The segmentation rules or standards may be preset by the segmentation model, and the rib segmentation may be performed on each CXR sample image according to the segmentation rules or standards. The loss function may be used to guide the training of the segmentation model, such as directing the optimization of the parameters of the segmentation model to ensure that the segmentation result meets the segmentation rules or standards. Once the loss function has converged, the parameters of the segmentation model may be stored and the segmentation model may be deployed to process CXR images.

It should be noted that the CXR sample images described herein may be historical CXR images in which the rib positions have been determined and/or labeled. The CXR sample images may also include simulated (e.g., computer-generated) sample images, and/or the like.

In some embodiments, training the rib segmentation model to segment a CXR sample image according to preset segmentation rules or standards may include training the rib segmentation model to perform first (e.g., primary) segmentation, second (e.g., secondary) segmentation, and third (e.g., tertiary) segmentations on the CXR sample image according to preset first, second, and third sets of segmentation rules or standards, respectively.

In some embodiments, optimizing the parameters of the rib segmentation model based on a loss function until the loss function converges may include optimizing the parameters of the segmentation model based on a first loss function associated with the first (e.g., primary) segmentation, optimizing the parameters of the segmentation model based on a second loss function associated with the second (e.g., secondary) segmentation, optimizing the parameters of the segmentation model based on a third loss function associated with the third (e.g., tertiary) segmentation, and/or optimizing the parameters of the segmentation model based on a fourth loss function associated with the entire segmentation task (e.g., the fourth loss function may be an end-to-end loss function that indicate a difference between the rib sequence predicted by the rib segmentation model and a ground truth for the rib sequence). In some embodiments, determining that the training has completed may include determining that the first, second, third and/or fourth loss functions have converged.

As described herein, various loss functions may be set and utilized during the training process. The loss functions may be the same or may be different. The first three loss functions may correspond to the primary segmentation, the secondary segmentation, and the tertiary segmentation, respectively, and the fourth loss function may correspond to the entire segmentation task. Optimization of the segmentation model may be performed at different levels, for example, by setting respective segmentation rules or standards or optimization targets for the multiple segmentation operations. Utilizing the hierarchical approach described herein may convert a single, complex segmentation task into multiple (e.g., three) sub-tasks having different levels of complexities and difficulties (e.g., from easy to difficult, or coarse to fine), thus reducing the challenges associated with the segmentation task and improving the accuracy of the segmentation operation. In some embodiments, the segmentation operations (e.g., the objectives, rules or standards set for the first, second, and third segmentation operations described herein) may include sequentially arranging the ribs identified in a CXR image. Such sequential arrangement may include determining the sequence order of the ribs (e.g., rib1, rib2, . . . rib12) based on the location of each subset or group of ribs in the CXR image and the location of each individual rib within the subset or group of ribs.

The lung field segmentation model described herein may be trained in a similar manner as the rib segmentation model.

In some embodiments, a chest image (e.g., a CXR image) may be obtained and the quality of the image may be determined in real time, for example, while a medical device configured to capture the chest image is in operation. The chest image (e.g., the CXR image) and the determined quality of the image may be stored (e.g., in a database) and subsequently (upon receiving a review instruction), the image and/or the quality of the image may be retrieved from the database, for example, according to a preset condition included in the review instruction.

As described herein, CXR images generated by a medical device may be acquired in real time while the medical device is in normal operation. The CXR quality may be determined in real time and provided to doctors or technicians during the scanning and image capturing process. The CXR images and the corresponding CXR quality information may be stored (e.g., in a database), and subsequently, CXR images scanned and captured under certain preset conditions may be reviewed and statistics about the CXR images may be gathered based on review instructions issued by a doctor or technician, such that the CXR operations may be subjected to standardized review and management.

In examples, the preset condition described herein may indicate a target medical device and/or a target time period, and CXR images retrieved from the database according to the preset condition may include CXR images scanned and captured by the target medical device and/or during the target time period. Various conditions may be added to or deleted from a predetermined set of conditions according to the needs of an actual application. For example, such preset conditions may not be limited to a target medical device and/or a target time period, and may include a specific doctor or technician that performs the CXR operation.

In some embodiments, a determination may be made, e.g., at a preset interval, regarding whether a chest image (e.g., an unprocessed CXR image) exists in an image archive or a communication system (e.g., a PACS system) associated with medical device. If the determination is that such an image exists, the image may be obtained and a quality of the image may be determined based on the techniques described herein. Further (e.g., after determining the quality of the image), one or more of the following may be performed: the image and the determined quality information may be stored in a database; a review instruction may be received; a preset condition may be determined according to the review instruction; and/or the image and/or quality of the image may be retrieved from the database according to the preset condition.

In certain circumstances (e.g., due to an accidental failure of a medical device or scanner), chest images (e.g., CXR images) may be captured but not processed (e.g., these images may be stored on a PACS). Quality determination and/or review may be performed for these unprocessed images at preset intervals, for example, to avoid missing important images. Upon performing the quality determination and/or review, the images and the corresponding quality information for the images may be stored in a database, and subsequently, a target image (e.g., a target CXR image scanned and captured under a preset condition) may be checked and statistics about the image may be gathered based on a review instruction issued by a doctor or technician. This way, chest scan and imaging operations may be subjected to standardized review and management.

It should be noted that the acquisition and quality control of chest images (e.g., CXR images) in real time and the acquisition and quality control of unprocessed chest images at preset intervals may be conducted on a same device (e.g., a medical scanner).

Figure 5:
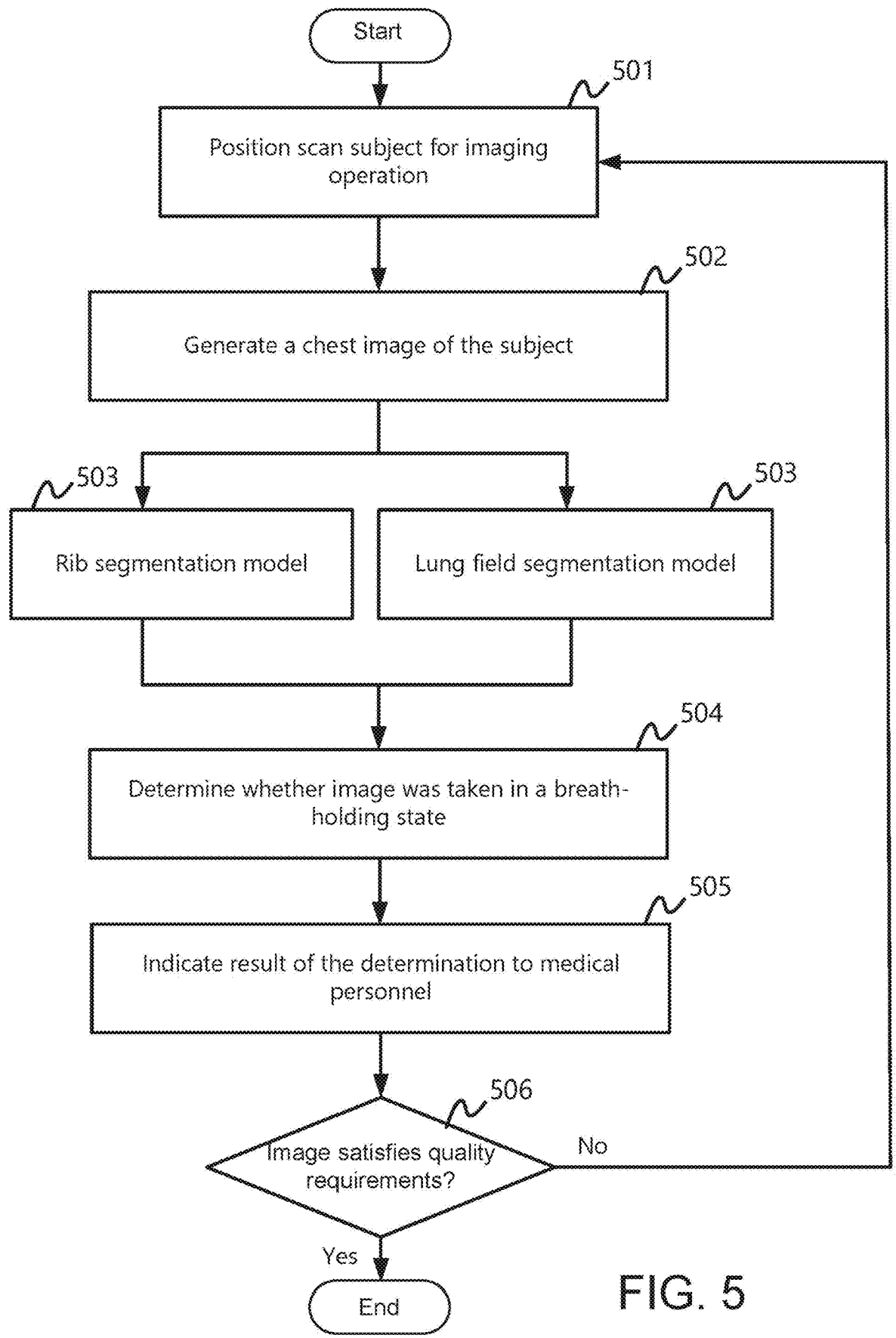
FIG. 5 is a diagram of an example workflow for performing real-time quality control over a CRX image taken at deep inspiration according to an embodiment described herein.

FIG. 5 illustrates an example process for processing of a chest image (e.g., performing quality control over whether the image is taken in a breath-holding state). At 501, a scan subject may be positioned for chest image capturing. At 502, a chest image such as a CXR image may be generated by an imaging device (e.g., an X-ray scanner). At 503, the captured image may be obtained in real time (e.g., from the imaging device) and provided to a processing engine on which the rib segmentation model and the lung field segmentation model described herein are implemented. At 504, a determination may be made regarding whether one or more designated ribs (e.g., such as the 10th rib) overlap with one or more lung fields identified in the chest image. If the determination is that the overlap exists, the chest image may be determined to comply with a scan protocol or specification; otherwise, the image may be determined to not comply (e.g., being inconsistent) with the scan protocol or specification. At 505, the evaluation result (e.g., whether the chest image complies with the scan protocol) may be provided (e.g., displayed) to medical personnel such as a technician or doctor, who may determine, at 506, whether the subject should be rescanned based on whether the image quality satisfies the scan protocol or specification.

Figure 6:
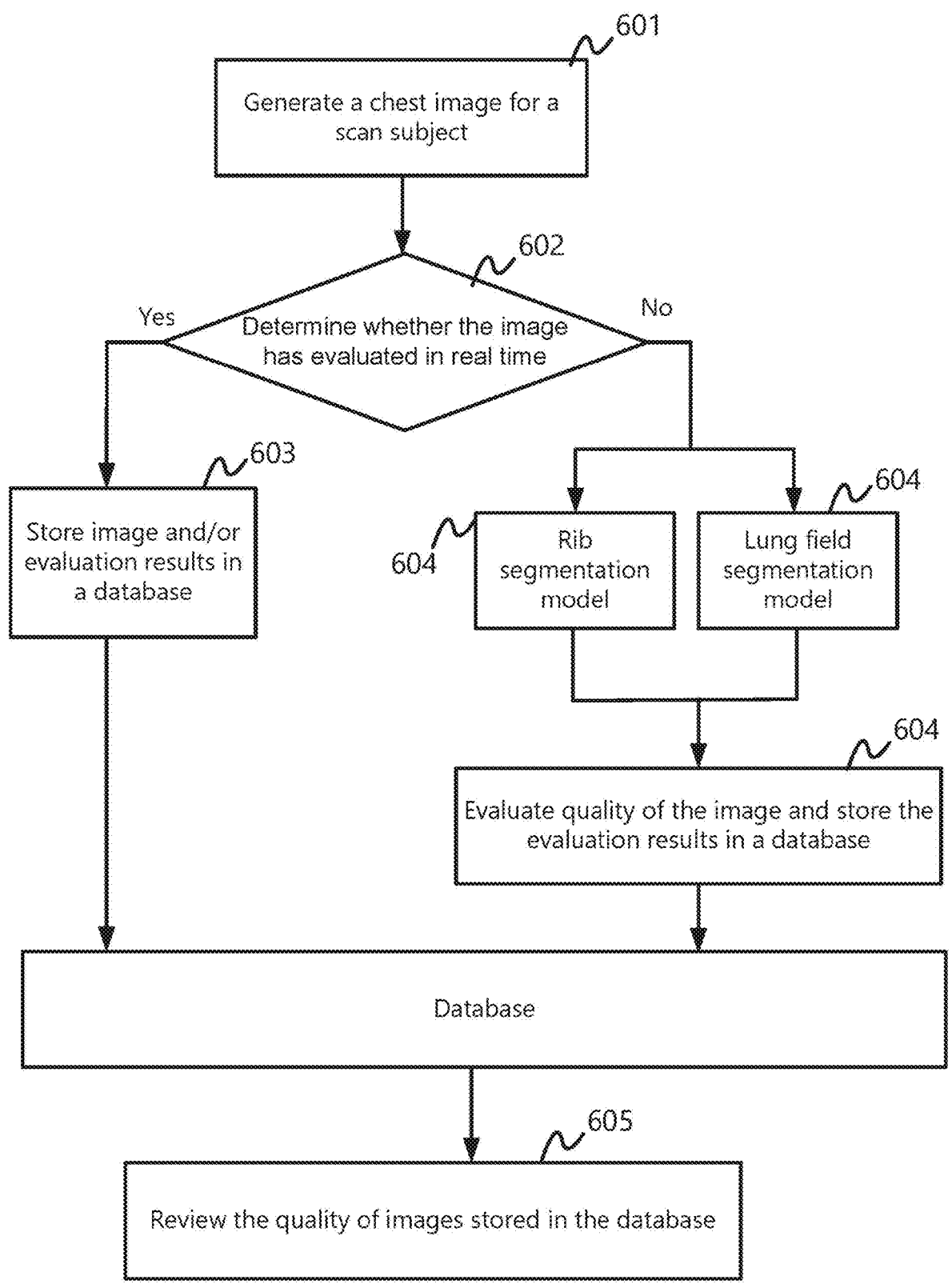
FIG. 6 is a diagram of an example workflow for performing retrospective quality control over CRX images taken at deep inspiration according to an embodiment described herein.

FIG. 6 shows an example workflow associated with performing retrospective quality control over one or more chest images (e.g., determining whether the images are taken in a breath-holding state). At 601, a chest image may be generated by a chest imaging device. At 602, a determination may be made regarding whether the chest image has already been evaluated (e.g., regarding whether the image was taken in a breath-holding state) by a real-time quality control system. If the determination is that the image has already been evaluated, the image may be stored in a database (e.g., a PACS) at 603. If the determination at 602 is that the image has not yet been evaluated, the image (e.g., which may be stored on a PACS) may be evaluated, at 604, using the rib segmentation model and the lung field segmentation model described herein at predetermined intervals, and the result of the evaluation may be save to the database. At 605, a user may review the images and/or evaluation results of the images that are stored in the database, for example, for a specific time period, a specific medical professional (e.g., a doctor or technician), and/or a specific imaging device.

In some embodiments, since the ribs in the human body may have high similarities, the segmentation model described herein may play the role of a classifier in a forward propagation process. Since a chest image may capture approximately 12 ribs, which may belong to a number of classes, segmenting all of the ribs directly may be difficult. The hierarchical classification or clustering approach described herein divides the segmentation task into multiple (e.g., three) sub-tasks (e.g., from easy to difficult or coarse to fine), combines the output of an easy sub-task with the original input image, and provide the combined information as an input of a subsequent, more complex sub-task. These sub-tasks may include a first sub-task in which all the ribs captured in an input image are segmented as one labeled object, a second sub-task in which the ribs (e.g., 12 ribs) are classified into three groups or classes (e.g., a first class corresponding to the 1st through 6th ribs, a second class corresponding to the 7th through 10th ribs, and/or a third class corresponding to the 11th through 12th ribs) for segmentation, and a third sub-task in which each individual rib is segmented (e.g., the 12 ribs are segmented as 12 individually labelled object) based on at least the results of the second sub-task.

Figure 7:
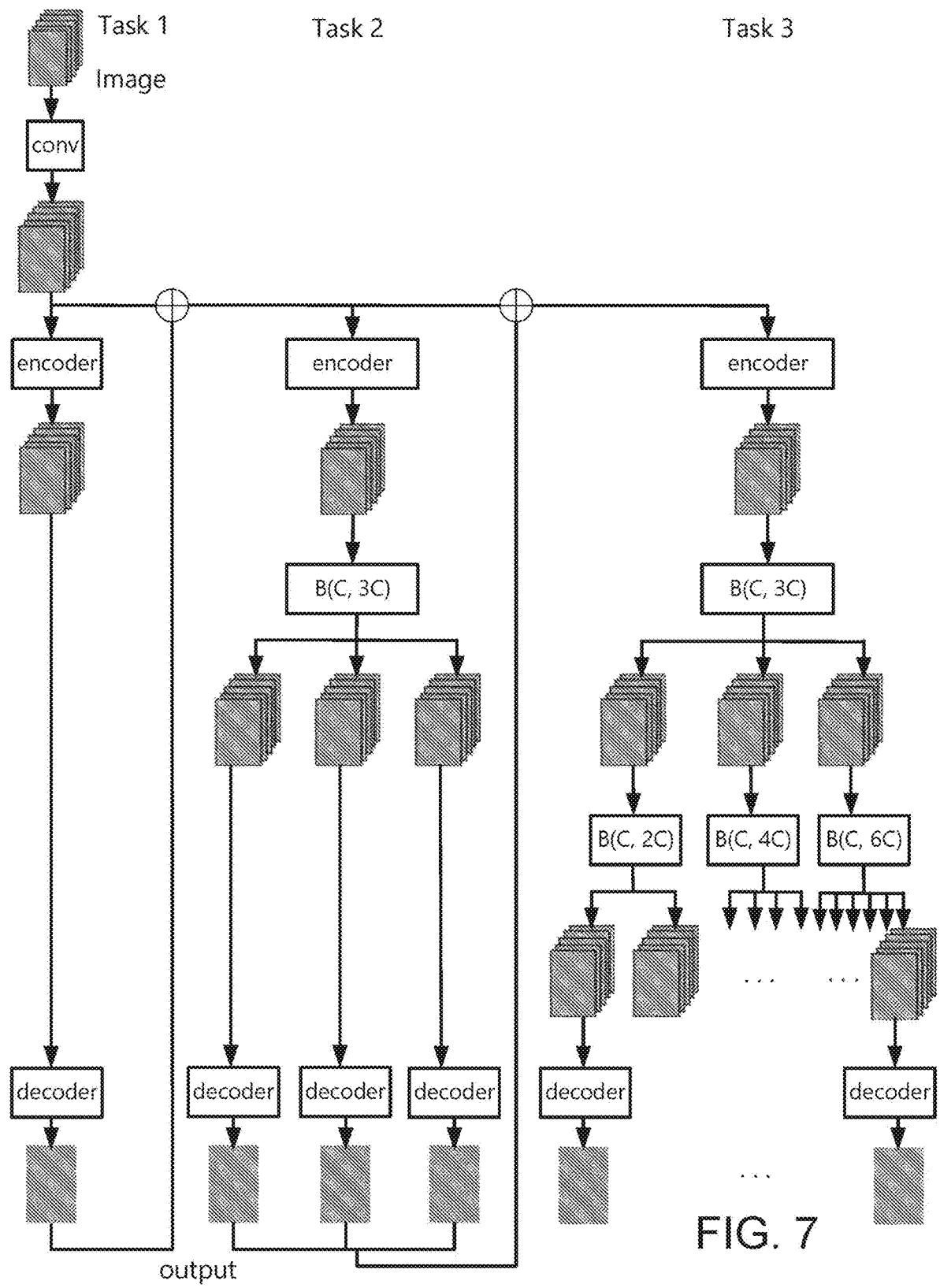
FIG. 7 is a schematic diagram of an example rib segmentation model according to an embodiment described herein.

FIG. 7 shows an example structure for the rib segmentation model described herein. The rib segmentation model may adopt an encoder-decoder structure (e.g., including a lightweight structure similar to that utilized by LinkNet) as the basic structure. In this structure, a non-local module integrating global information may be coupled with or included in the decoder. B(C, 3C), etc. shown in FIG. 7 may denote a BottleNeck structure, through which one or more classification operations may be accomplished.

During training of the rib segmentation model, a training image such as aa CXR image may be provided as an input to the model, and ground truth associated with the three tasks may be obtained (e.g., in the forms of label1, label2, label3). Each of the three tasks may produce an output (e.g., output output1, output2, output3), and a respective loss function may be set and computed for each task such as loss1 (output1, label1), loss2 (output2, label2), and loss3 (output3, label3). Optimization of the model parameters may then be performed by converging the loss functions (e.g., in an order of easy to difficult). For example, the optimization may be accomplished by converging loss1 first, followed by the convergence of loss2 and loss3, and (e.g., finally) an end-to-end loss function that considers the three loss functions jointly. In an actual inference process, output3 may correspond to the segmentation result (e.g., indicating the sequence number of each rib) output by the neural network.

Figure 8:
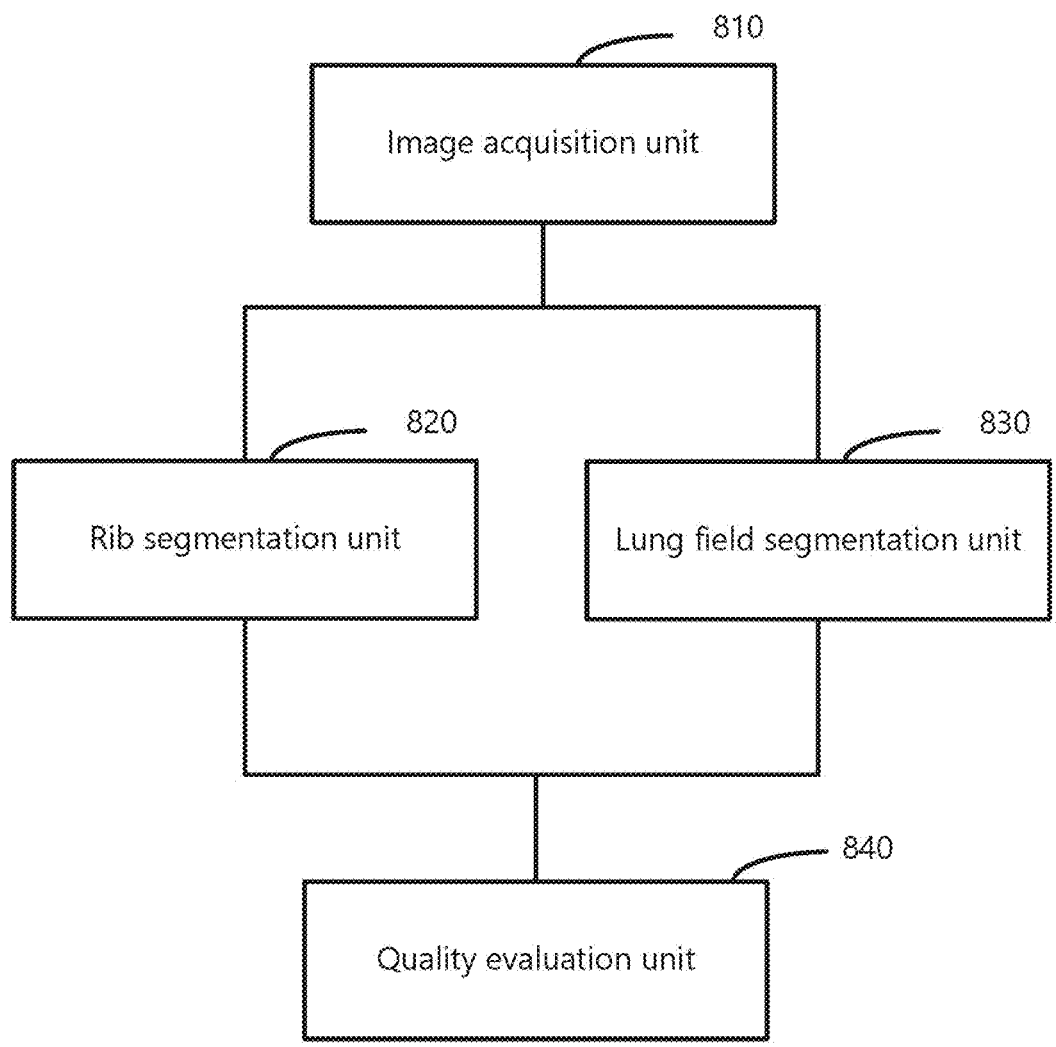
FIG. 8 is a schematic diagram of an example system for processing a CXR image according to an embodiment described herein.

A system or apparatus for processing chest images (e.g., CXR images) may be implemented in accordance with the techniques described herein. FIG. 8 is a schematic diagram of an example system (or apparatus) for processing a CXR image according to one or more embodiment. As shown, the system may include an image acquisition unit 810 configured to obtain a CXR image produced by a medical device, a rib segmentation unit 820 configured to receive the CXR image and provide the image to a pre-learned rib segmentation model to obtain a rib segmentation result (e.g., the result may be output by the rib segmentation model and may include an identified rib sequence), a lung field segmentation unit 830 configured to receive the CXR image and provide the image to a pre-learned lung field segmentation model to obtain a lung field segmentation result (e.g., the result may be output by the lung field segmentation model and may indicate one or more lung field identified in the CXR image), and/or a quality evaluation unit 840 configured to determine whether one or more ribs (e.g., a predetermined set of one or more specific ribs) overlap with the lung fields according to the rib segmentation result and the lung field segmentation result, and determine the quality of the CXR image based on the overlap (or the lack thereof).

Using the system (or apparatus) shown in FIG. 8 (e.g., including the image acquisition unit 810, the rib segmentation unit 820, the lung field segmentation unit 830, and/or the quality evaluation unit 840), a chest image such as a CXR image may be obtained by the image acquisition unit 810, for example, from a medical device configured to capture the CXR image. The CXR image may be provided as an input to the rib segmentation model 820 and the lung-field segmentation model 830, respectively, so as to obtain a rib segmentation result and a lung field segmentation result, respectively. As described herein, the rib segmentation result may include an identified rib sequence (e.g., rib locations and/or sequence numbers) and the lung field segmentation result may include one or more identified lung fields. The quality evaluation unit 840 may determine whether a predetermined set of specific ribs overlap with the lung fields by combining and/or comparing the two segmentation results, and further determine a quality of the CXR image based on whether the specific ribs overlap with the lung fields. As described herein, whether the specific ribs overlap with the lung fields in the CXR image may be determined by analyzing and processing (e.g., segmenting) the CXR image, and the quality of the CXR image (e.g., whether the scan subject was in a breath-holding state during the CXR imaging process) may be determined automatically (e.g., without requiring a doctor or technician to manually evaluate the image). Waiting time for scan subjects as well as the effectiveness and speed of CXR imaging operations may be improved as a result.

In some embodiments, the quality evaluation unit 540 may be configured to, based on a determination that the predetermined set of specific ribs overlap with the lung fields, provide an indication (e.g., to a doctor or technician) that the CXR image is a qualified CXR, and, based on a determination that the specific ribs do not overlap with the lung fields, provide an indication that the CXR image is a secondary CXR image (e.g., having a quality lower than that of a qualified CXR image).

In some embodiments, the quality evaluation unit 540 may be configured to, based on a determination that the specific ribs overlap with the lung fields, determine the number of ribs that overlap with the lung fields. If the determined number is within a preset value or number range, the quality evaluation unit 540 may provide an indicate that the CXR image is a qualified CXR image.

In some embodiments, the rib segmentation unit 520 may be configured to identify the ribs in the CXR image using the rib segmentation model, and perform a first (e.g., primary) segmentation to delineate a first region where all the ribs are estimated to be located as a labelled region. The rib segmentation unit 520 may perform a second (e.g., secondary) segmentation on the first region (e.g., on the ribs in the labelled first region) to obtain a plurality of rib set regions with corresponding classes. The rib segmentation unit 520 may then perform a third (e.g., tertiary) segmentation on each of the rib set regions to determine the location (e.g., bounds and/or contours) of each individual rib in the rib set region, and to sequentially arrange the ribs (e.g., by assigning sequence numbers to the ribs) according to the position of each rib in a corresponding rib set region and the position of each rib set region in the CXR image. The rib segmentation result may indicate the locations of the individual ribs and their corresponding sequence numbers.

Figure 9:
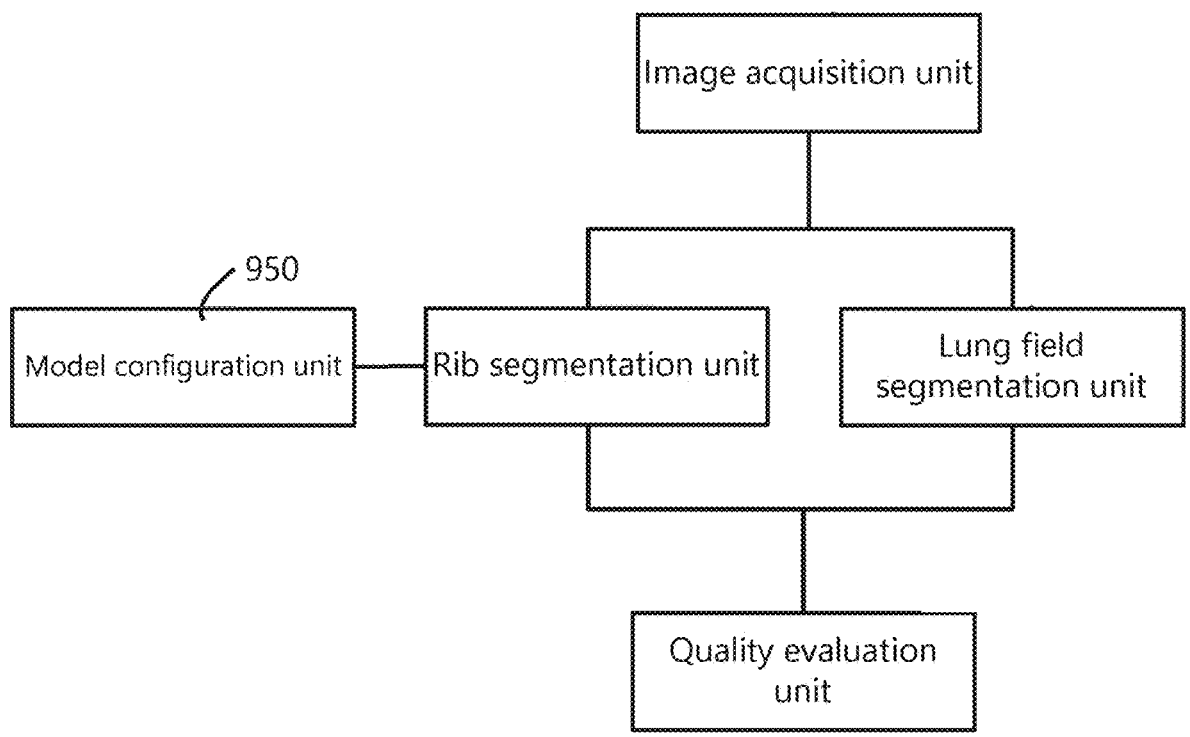
FIG. 9 is a schematic diagram of an example system for processing a CXR image according to another embodiment described herein.

In some embodiments, the system (or apparatus) described herein for processing a chest image may further include a model configuration unit (e.g., as shown in FIG. 9) that is configured to acquire (e.g., learn) the rib segmentation model described herein. In examples, the model configuration unit (e.g., 950 in FIG. 9) may be configured with an initialized segmentation model (e.g., a multi-label segmentation model) and may be provided with a plurality of CXR sample images for training purposes. The model configuration unit may provide each of the CXR sample images as an input to the segmentation model, and perform a rib segmentation on the input CXR sample image using the segmentation model according to preset segmentation rules or standards. The model configuration unit may determine, based on a loss function, a loss associated with the rib segmentation and optimize the parameters of the segmentation model until the loss function converges (e.g., through a backpropagation process). The model configuration unit may take the parameters of the segmentation model at the time of the convergence as the parameters of the segmentation model, and take the segmentation model as the preset rib segmentation model described herein.

In some embodiments, the model configuration unit 950 may be configured to perform a first (e.g., primary) segmentation, a second (e.g., secondary) segmentation, and a third (e.g., tertiary) segmentation on each of the CXR sample images using the segmentation model according to three sets of segmentation rules or standards. The model configuration unit may optimize (e.g., sequentially) respective loss functions for the primary segmentation, the secondary segmentation, and the tertiary segmentation. The model configuration unit may also optimize a fourth loss function (e.g., an end-to-end loss function) associated with the whole segmentation process.

Figure 10:
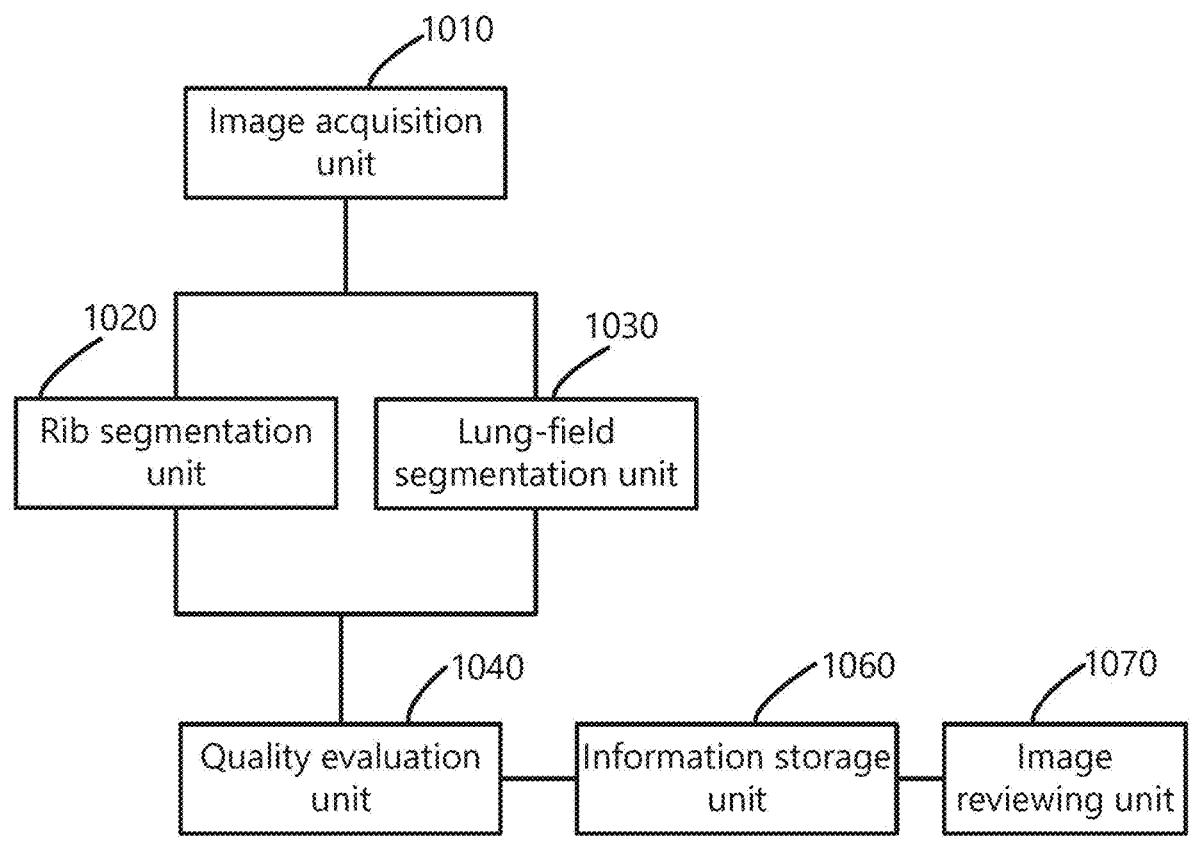
FIG. 10 is a schematic diagram of an example system for processing a CXR image according to yet another embodiment described herein.

FIG. 10 shows another example system (or apparatus) for processing chest images. As shown, the system may include an image acquisition unit 1010 configured to acquire CXR images in real time (e.g., during the normal operation of an chest imaging device), a rib segmentation unit 1020 as described herein, a lung field segmentation unit 1030 as described herein, and quality evaluation unit 1040 as described herein. The system may further include an information storage unit 1060 configured to store CXR images and corresponding CXR quality information (e.g., in a database); and an image review unit 1070 configured to receive a review instruction, determine a preset condition according to the review instruction, and retrieve and/or display the quality of one or more target CXR images from the database according to the preset condition.

In some embodiments, the image acquisition unit 1010 may be configured to determine, at preset intervals, whether an unprocessed CXR image exists on a PACS associated with a medical device. If the determination is that such a CMR image exists, the image acquisition unit 1010 may obtain the unprocessed CXR image so that the image may be processed using the rib segmentation unit 1020, the lung field segmentation unit 1030, and/or the quality evaluation unit 1040.

The information storage unit 1060 may be configured to store the CXR image processed by the rib segmentation unit 1020, the lung field segmentation unit 1030, and/or the quality evaluation unit 1040. The information storage unit 1060 may be further configured to store the corresponding CXR quality information of the CXR image to the database. The image reviewing unit 1070 may be configured to receive a review instruction, determine a preset condition according to the review instruction, and retrieve and/or display the quality information for one or more target CXR images from the database according to the preset condition.

The system or apparatus for processing a chest image (e.g., a CXR image) according to the embodiments described herein correspond to the methods for processing the chest image described herein. The technical features and the beneficial effects described in the embodiments of the above-mentioned methods for processing a CXR image are similarly applicable to the embodiments of the system or apparatus for processing the CXR image. The embodiments described herein are also applicable to a readable storage medium having one or more executable programs stored thereon, and the executable program(s) may be executed by a processor to implement the steps of the above-mentioned methods for processing a CXR image.

With the executable program(s) stored in the above-mentioned readable storage medium, whether one or more ribs overlap with a lung field identified in a chest image (e.g., a CXR image) may be determined by analyzing and processing the chest image using machine-learned segmentation models, so as to determine the quality of the chest image including whether the scan subject is in a breath-holding state during the chest imaging process. As a result, whether the scan subject is in a breath-holding state does not need to be evaluated by a doctor or a technician, and may instead be evaluated directly by assessing the quality of the chest image. Hence, the waiting time of patients may be shortened and the effectiveness and speed of chest imaging procedures may be improved.

The embodiments described herein are also applicable to a device for processing a chest image (e.g., a CXR image). Such a device may include a memory for storing one or more executable programs, and a processor configured to, by executing the one or more executable programs, implement the steps of the above-mentioned methods for processing the chest image.

By running the executable program(s) on the processor of the above-mentioned device, whether one or more ribs overlap with a lung field identified in the chest image may be determined by analyzing and processing the image using machine-learned segmentation models, so as to determine the quality of the chest image. As a result, whether the scan subject is in a breath-holding state during the chest imaging process does not need to be evaluated by a doctor or technician, and may instead be determined directly by assessing to quality of the chest image. Hence, the waiting time of patients may be shortened and the effectiveness and speed of chest imaging procedures may be improved. The device for processing a chest image may be provided in the system 100, the terminal device 130, or the processing engine 140 shown in FIG. 1.

Those skilled in the art may understand that all or part of the workflow described herein for the chest image processing methods may be implemented by a computer program and hardware controlled by the program. The program may be stored in a non-volatile (e.g., non-transitory) computer readable storage medium such as the storage medium of a computer system described in some embodiments. When executed by at least one processor in the computer system, the program may implement the workflow of the above-mentioned methods according to the embodiments described herein. The storage medium may be a magnetic disk, an optical disk, a ROM, or a RAM, or the like.

The foregoing technical characteristics of the embodiments may be combined in any suitable manner. For ease of description, not all possible combinations of the technical characteristics in the foregoing embodiments are described. However, as long as a combination of the technical characteristics does not conflict with disclosure provided herein, the combination may be considered to be within the scope of this disclosure.

Those skilled in the art may appreciate that all or part of the steps in the above-mentioned methods may be implemented by a program instructing related hardware. The program may be stored in the readable storage medium. The program, when executed, may perform the steps of the above-mentioned methods. The storage medium may include a ROM/RAM, a magnetic disk, an optical disk, or the like.

The foregoing embodiments only describe example implementations of the present disclosure. While some descriptions may be specific and detailed, they should not be understood as limiting the scope of the present disclosure. A person of ordinary skills in the art may further make modifications and improvements to the disclosure without departing from the fundamentals of the present disclosure, and these modifications and improvements shall fall within the scope of the present disclosure, which may be illustrated by the claims appended herein.

What is claimed is:

1. A method for processing medical chest images, the method comprising:
   obtaining a chest image;

segmenting the chest image based on a machine-learned rib segmentation model to obtain a rib segmentation result, wherein the rib segmentation result indicates a rib sequence identified in the chest image, and wherein segmenting the chest image based on the machine-learned rib segmentation model comprises:
  segmenting the chest image to determine a first region that is estimated to enclose a plurality of ribs identified in the chest image;
  segmenting the first region to determine one or more second regions, wherein each of the one or more second regions is associated with a respective subset of the plurality of ribs enclosed in the first region; and
  segmenting each of the one or more second regions to identify individual ribs located in the each of the one or more second regions;
segmenting the chest image based on a machine-learned lung field segmentation model to obtain a lung field segmentation result, wherein the lung field segmentation result indicates one or more lung fields identified in the chest image;
determining, whether a predetermined set of one or more specific ribs overlaps with the one or more lung fields according to the rib segmentation result and the lung field segmentation result; and
determining a quality of the chest image in accordance with whether the predetermined set of one or more specific ribs overlaps with the one or more lung fields.

2. The method according to claim 1, wherein the quality of the chest image is determined to meet a quality requirement if the predetermined set of one or more specific ribs overlaps with the one or more lung fields, and wherein the quality of the chest image is determined to fail the quality requirement if the predetermined set of one or more specific ribs does not overlap with the one or more lung fields.

3. The method according to claim 2, wherein determining whether the predetermined set of one or more specific ribs overlaps with the one or more lung fields comprises determining a number of ribs that overlaps with the one or more lung fields, and wherein the quality of the chest image is determined to meet the quality requirement if the number of ribs that overlaps with the one or more lung fields is within a preset value range.

4. The method of claim 1, wherein segmenting the chest image based on the machine-learned rib segmentation model further comprises determining respective sequence numbers of the individual ribs based on respective locations of the one or more second regions and respective locations of the individual ribs within a corresponding one of the one or more second regions, and wherein the rib segmentation result further indicates the respective locations of the individual ribs.

5. The method according to claim 1, wherein the rib segmentation model is learned through at least the following steps:
  initializing parameters of the rib segmentation model;
  for each of a plurality of chest training images:
    segmenting the chest training image using the rib segmentation model; and
    adjusting the parameters of the rib segmentation model based on a loss function that indicates a difference between an actual result of the segmentation and a desired result;
  determining that the loss function has converged; and
  responsive to determining that the loss function has converged, storing the parameters of the rib segmentation model.

6. The method according to claim 5, wherein, for each of the plurality of chest training images, segmenting the chest training image using the rib segmentation model comprises:
  segmenting the chest training image using the rib segmentation model to determine a first rib area, wherein the first rib area is estimated to enclose a plurality of ribs in the chest training image;
  segmenting the first rib area using the rib segmentation model to determine one or more second rib areas, wherein each of the one or more second rib areas is estimated to enclose a respective subset of the plurality of ribs in the chest training image;
  segmenting each of the one or more second rib areas using the rib segmentation model to determine one or more individual ribs within the each of the one or more second rib areas; and
  determining respective sequence numbers of the one or more individual ribs based on respective locations of the one or more second rib areas in the chest training image and respective locations of the one or more individual ribs within a corresponding one of the one or more second rib areas.

7. The method according to claim 6, wherein, for each of the plurality of chest training images, adjusting the parameters of the rib segmentation model based on the loss function comprising:
  making first adjustments to the parameters of the rib segmentation model based on a first loss function that indicates a difference between the first rib area and a ground truth for the first rib area;
  making second adjustments to the parameters of the rib segmentation model based on a second loss function that indicates a difference between each of the one or more second rib areas and a ground truth for the each of the one or more second rib areas;
  making third adjustments to the parameters of the rib segmentation model based on a third loss function that indicates a difference between the one or more individual ribs within each of the one or more second rib areas and a ground truth for the one or more individual ribs within the each of the one or more second rib areas; and
  making fourth adjustments to the parameters of the rib segmentation model based on a fourth loss function that indicates a difference between the individual ribs identified in the chest training image and a ground truth for the individual ribs in the chest training image.

8. The method of claim 7, wherein determining that the loss function has converged comprises determining that each of the first, second, third, and fourth loss functions has converged.

9. The method according to claim 1, wherein the quality of the chest image is determined in real time during normal operations of a medical device configured to capture the chest image; and wherein the method further comprises:
  storing the chest image and corresponding quality information of the chest image to a database;
  receiving a review instruction;
  determining a preset condition according to the review instruction; and
  acquiring quality information associated with one or more target chest images from the database according to the preset condition.

10. The method according to claim 9, wherein the preset condition indicates at least one of a time duration, a specific medical imaging device, or the identify of a medical professional.

11. An apparatus configured to process medical chest images, comprising:
one or more processors configured to:
obtain a chest image;
segment the chest image based on a machine-learned rib segmentation model to obtain a rib segmentation result, wherein the rib segmentation result indicates a rib sequence identified in the chest image, and wherein the one or more processors being configured to segment the chest image based on the machine-learned rib segmentation model comprises the one or more processors being configured to:
segment the chest image to determine a first region estimated to enclose a plurality of ribs identified in the chest image;
segment the first region to determine one or more second regions, wherein each of the one or more second regions is associated with a respective subset of the plurality of ribs enclosed in the first region; and
segment each of the one or more second regions to identify individual ribs located in the each of the one or more second regions;
segment the chest image based on a machine-learned lung field segmentation model to obtain a lung field segmentation result, wherein the lung field segmentation result indicates one or more lung fields identified in the chest image;
determine, based on the rib segmentation result and the lung field segmentation result, whether a predetermined set of one or more specific ribs overlaps with the one or more lung fields in the chest image; and
determine a quality of the chest image in accordance with whether the predetermined set of one or more specific ribs overlaps with the one or more lung fields.

12. The apparatus of claim 11, wherein the one or more processors are configured to determine that the quality of the chest image meets a quality requirement if the predetermined set of one or more specific ribs overlaps with the one or more lung fields, the one or more processors further configured to determine that the quality of the chest image fails the quality requirement if the predetermined set of one or more specific ribs does not overlap with the one or more lung fields.

13. The apparatus of claim 11, wherein the one or more processors are configured to determine respective sequence numbers of the individual ribs based on respective locations of the one or more second regions and respective locations of the individual ribs within a corresponding one of the one or more second regions, and wherein the rib segmentation result further indicates the respective locations of the individual ribs.

14. The apparatus of claim 11, wherein the rib segmentation model is learned via one or more computing devices that are configured to:
initialize parameters of the rib segmentation model;
for each of a plurality of chest training images:
segment the chest training image using the rib segmentation model; and
adjust the parameters of the rib segmentation model based on a loss function that indicates a difference between a result of the segmentation and a desired result;
determine that the loss function has converged; and
responsive to the determination that the loss function has converged, store the parameters of the rib segmentation model.

15. The apparatus of claim 14, wherein, for each of the plurality of chest training images, the one or more computing devices being configured to segment the chest training image using the rib segmentation model comprises the one or more computing devices being configured to:
segment the chest training image using the rib segmentation model to determine a first rib area, wherein the first rib area is estimated to enclose a plurality of ribs identified in the chest training image;
segment the first rib area using the rib segmentation model to determine one or more second rib areas, wherein each of the one or more second rib areas is estimated to enclose a respective subset of the plurality of ribs identified in the chest training image;
segment each of the one or more second rib areas using the rib segmentation model to determine one or more individual ribs within the each of the one or more second rib areas; and
determine respective sequence numbers of the one or more individual ribs based on respective locations of the one or more second rib areas in the chest training image and respective locations of the one or more individual ribs within a corresponding one of the one or more second rib areas.

16. The apparatus of claim 15, wherein, for each of the plurality of chest training images, the one or more computing devices being configured to adjust the parameters of the rib segmentation model based on the loss function comprising the one or more computing devices being configured to:
make first adjustments to the parameters of the rib segmentation model based on a first loss function that indicates a difference between the first rib area and a ground truth for the first rib area;
make second adjustments to the parameters of the rib segmentation model based on a second loss function that indicates a difference between each of the one or more second rib areas and a ground truth for the each of the one or more second rib areas;
make third adjustments to the parameters of the rib segmentation model based on a third loss function that indicates a difference between the one or more individual ribs within each of the one or more second rib areas and a ground truth for the one or more individual ribs within the each of the one or more second rib areas; and
make fourth adjustments to the parameters of the rib segmentation model based on a fourth loss function that indicates a difference between the individual ribs identified in the chest training image and a ground truth for the individual ribs in the chest training image.

17. The apparatus of claim 11, wherein the one or more processors are configured to determine the quality of the chest image in real time during normal operations of a medical device configured to capture the chest image, the one or more processors further configured to:
store the chest image and corresponding quality information of the chest image to a database;
receive a review instruction;
determine a preset condition according to the review instruction; and
acquire quality information associated with one or more target chest images from the database according to the preset condition.

18. A method for training a rib segmentation model, the method comprising:

initializing parameters of the rib segmentation model; and for each of a plurality of chest training images:

performing a first segmentation of the chest training image using the rib segmentation model to determine a first rib area, wherein the first rib area is estimated to enclose a plurality of ribs identified in the chest training image;

performing a second segmentation of the first rib area using the rib segmentation model to determine one or more second rib areas, wherein each of the one or more second rib areas is estimated to enclose a respective subset of the plurality of ribs identified in the chest training image;

performing a third segmentation of each of the one or more second rib areas using the rib segmentation model to determine one or more individual ribs within the each of the one or more second rib areas; and adjusting the parameters of the rib segmentation model based at least on respective loss functions associated with the first segmentation, the second segmentation and the third segmentation.

\* \* \* \* \*